(12) United States Patent
Hoon et al.

(10) Patent No.: US 7,588,894 B2
(45) Date of Patent: Sep. 15, 2009

(54) USE OF ID4 FOR DIAGNOSIS AND TREATMENT OF CANCER

(75) Inventors: Dave S. B. Hoon, Los Angeles, CA (US); Naoyuki Umetani, Tokyo (JP)

(73) Assignee: John Wayne Cancern Institute, Santa Monica, CA (US)

( * ) Notice: Subject to any disclaimer, the term of this patent is extended or adjusted under 35 U.S.C. 154(b) by 0 days.

(21) Appl. No.: 11/345,836

(22) Filed: Feb. 1, 2006

(65) Prior Publication Data

US 2007/0020646 A1   Jan. 25, 2007

Related U.S. Application Data

(60) Provisional application No. 60/649,650, filed on Feb. 1, 2005.

(51) Int. Cl.
    C12Q 1/68    (2006.01)
    C07H 21/02   (2006.01)
    C07H 21/04   (2006.01)

(52) U.S. Cl. .................. 435/6; 536/23.1; 536/24.3

(58) Field of Classification Search .............. 435/6; 536/23.1, 24.3
    See application file for complete search history.

(56) References Cited

OTHER PUBLICATIONS

Rebhan, M., Chalifa-Caspi, V., Prilusky, J., Lancet, D.: GeneCards: encyclopedia for genes, proteins and diseases. Weizmann Institute of Science, Bioinformatics Unit and Genome Center (Rehovot, Israel), 1997. GeneCard for [ID4] [Mar. 22, 2007]).*

Fong, et al. Trends in Molecular Medicine 2004; 10(8): 387-392.*

Das, et al. Journal of Clinical Oncology, 2004; 22(22):4632-4642.*

Perk, et al. Nature Reviews Cancer 2005; 5:603-614.*

Umetani, et al. Clin Cancer Res 2004; 10:7475-7483.*

Umetani, et al. Oncogene 2005; 24:4721-4727.*

Chan, et al. Oncogene 2003; 22:6946-6953.*

Rigolet et al. cDNA cloning, tissue distribution and chromosomal localization of the human ID4 gene. DNA Research 5(5) : 309-313 (1998).*

Riechmann et al., "Mutually Exclusive Expression of Two Dominant-Negative Helix-Loop-Helix (dnHLH) Genes, Id4 and Id3, in the Developing Brain of the Mouse Suggests Distinct Regulatory Roles of these dnHLH Proteins During Cellular Proliferation and Differentiation of the Nervous System," *Cell Growth & Differentiation*, (1995), vol. 6, pp. 837-843.

Welcsh et al., "BRCA1 Transcriptionally Regulates Genes Involved in Breast Tumorigenesis," *Proc. Natl. Acad. Sci. USA*, (2002), vol. 99, pp. 7560-7565.

Beger et al., "Identification of Id4 as a Regulator of BRCA1 Expression by Using a Ribozyme-Library-Based Inverse Genomics Approach," *Proc. Natl. Acad. Sci. USA*, (2001), vol. 98, pp. 130-135.

Shan et al., "Id4 Regulates Mammary Epithelial Cell Growth and Differentiation and is Overexpressed in Rat Mammary Gland Carcinomas," *Am. J. Pathol.*, (2003), vol. 163, pp. 2495-2502.

Umetani et al., "Allelic Imbalance of APAF-1 Locus at 12q23 is Related to Progression of Colorectal Carcinoma," *Oncogene*, (2004), vol. 23, pp. 8292-8300.

Pagliuca et al., "Molecular Cloning of ID4, a Novel Dominant Negative Helix-Loop-Helix Human Gene on Chromosome 6p21.3-p22," *Genomics*, (1995), vol. 27, pp. 200-203.

* cited by examiner

*Primary Examiner*—Ethan Whisenant
(74) *Attorney, Agent, or Firm*—Hogan & Hartson LLP

(57) ABSTRACT

Methods for diagnosis and treatment of cancer using ID4 are disclosed. Specifically, epigenetic inactivation of ID4 in colorectal carcinomas and breast correlates with poor differentiation and unfavorable prognosis. Further, aberrant hypermethylation of ID4 gene promoter region increases risk of metastasis in colorectal and breast cancer.

16 Claims, 10 Drawing Sheets

USE OF ID4 FOR DIAGNOSIS AND TREATMENT OF CANCER

RELATED APPLICATION

This application claims priority to U.S. Provisional Application Ser. No. 60/649,650, filed Feb. 1, 2005, the content of which is incorporated herein by reference in its entirety.

This invention was made with support in part by grants from National Cancer Institute (PO CA 29605 Project II) and US Army (DOD Breast Grant). Therefore, the U.S. government has certain rights.

FIELD OF THE INVENTION

The present invention relates to inhibitors of DNA binding proteins. More specifically, the invention relates to use of ID4 for diagnosis and treatment of cancer.

BACKGROUND OF THE INVENTION

In the development of colorectal cancer (CRC), tumorsuppressor genes such as APC, p53, and genes on chromosome 18q (DCC, SMAD2, and DPC4/SMAD4) are inactivated by mutations or by chromosomal deletions (1, 2). Some CRCs have microsatellite instability caused by inactivation of mismatch repair genes such as hMSH2 or hMLH1 (3). In addition, epigenetic inactivation by hypermethylation of promoter regions of various tumor suppressor genes such as p16, APC, VHL, and hMLH1 have been found in CRCs (4-10) and used as molecular markers of CRC (11, 12).

Methylation of cytosines in CpG islands in the promoter region affects promoter activity and can down-regulate gene transcription (5). Because the promoter hypermethylation of genes in cancer cells is as significant as deletions or mutations (13-15), hypermethylation of key regulatory genes can play a significant role in transformation and tumor progression. Progression of transformed cells requires regulatory gene inactivation that promotes growth, dedifferentiation, invasion, and/or metastasis.

Transcription factors containing a basic helix-loop-helix (bHLH) motif regulate the expression of certain tissue-specific genes (16) and have important roles in cell differentiation and embryonic developmental processes. DNA-binding activity of the bHLH proteins is dependent on formation of homo- and/or heterodimers. ID family proteins, which are distinct members of the helix-loop-helix (HLH) protein family, contain the HLH-dimerization domain but lack the DNA-binding basic domain. Consequently, ID proteins dominantly inhibit binding to DNA and transcriptional transactivation by forming heterodimers with bHLH proteins and modulate various key developmental processes (17). Currently, four known human ID proteins have been identified. Expression studies have shown that ID proteins play critical roles in early embryonic development (18-20). They are also involved in angiogenesis, lymphocyte development, cell cycle control, and cellular senescence (21-23). The involvement of ID proteins in neoplastic processes has been suggested. Increased ID1 and ID2 expression has been reported in various tumor types, including adenocarcinomas arising from the colon and pancreas (24, 25). Transgene expression of ID1 and ID2 in mice has resulted in tumor formation in the intestinal epithelium and lymphoid organs, respectively (26, 27). Expression of ID3 has been more variable; studies report both up-regulation (24, 28) and down-regulation (29, 30) in different tumor types.

ID4 gene has a relation with growth and differentiation of cells, as reported with oligodendrocytes (31). Recently, it was reported that ID4 promoter is hypermethylated in 30% of primary gastric cancers, and expression is down-regulated in most gastric cancer cell lines by hypermethylation of the promoter region (32). Despite the structural similarity, ID4 is known to have some differences from the other three known ID gene members. Unlike ID1, ID2, and ID3, the immunoreactivity of which is significantly elevated in CRCs compared with normal epithelium (24), ID4 has a more restricted expression pattern during murine and avian embryogenesis and is expressed at more advanced stages of differentiation in tissues (18-20). In the development of murine stomach, ID4 expression is restricted to the ventral part where cells grow slower, whereas other ID members are expressed in the dorsal part of the stomach where cells proliferate faster (18). Information about ID4 function, expression, and regulation of tumor progression is very limited, and there are no published studies of ID4 in CRC to date.

The presence of axillary lymph node metastases is the most significant prognostic factor for patients with breast cancer (Fisher et al., 1993; Fitzgibbons et al., 2000). For patients with early breast cancers, the ability to predict nodal metastasis could alleviate the need for axillary staging. The rate of nodal metastasis in T1 ($\geqq 2.0$ cm) breast cancers is reportedly from 18% to 31% (Barth et al., 1997; Carter et al., 1989; Holland et al., 1996). There are several known risk factors of lymph node metastasis for invasive breast cancer to date. For nodal metastasis of T1 breast cancer, lymphovascular invasion, tumor size, histologic grade, histologic type, and estrogen receptor (ER) status are the major risk factors of pathological findings (Brenin et al., 2001).

Advanced breast cancers reportedly express ID1 (Lin et al., 2000; Singh et al., 2002), and ID1 expression is associated with poor clinical outcome of patients with node-negative breast cancer (Schoppmann et al., 2003). By contrast, expression of ID2 is low in invasive breast cancer and correlates with noninvasive phenotype (Itahana et al., 2003). Expression of ID3 or ID4 in breast cancer has not been well studied. In breast cancer, animal studies have demonstrated that ID4 regulates mammary epithelial cell growth and differentiation, and overexpression of this protein in rat mammary gland carcinomas correlates with proliferation, invasiveness, and tumor weight (Shan et al., 2003). However, certain human primary breast cancers reportedly have low or no expression of ID4 protein by immunohistochemistry (IHC) (Welcsh et al., 2002), suggesting downregulation of the ID4 gene.

SUMMARY OF THE INVENTION

This invention relates to methods for diagnosis and treatment of cancer using ID4.

In one aspect, the invention features a method of determining whether a subject is suffering from or at risk for developing colorectal cancer. The method comprises obtaining a biological sample from a subject and determining the methylation level of an ID4 gene promoter, the expression level of an ID4 gene, or a combination thereof in the sample. The methylation level of the ID4 gene promoter in the sample higher than a control methylation level, the expression level of the ID4 gene in the sample lower than a control expression level, or a combination thereof indicates that the subject is likely to be suffering from or at risk for developing colorectal cancer. In one embodiment, the subject may be suffering from or at risk for developing primary or metastatic colorectal cancer.

In another aspect, the invention features a method of determining the histopathological grade of colorectal cancer. The method comprises obtaining a biological sample (e.g., a benign or primary colorectal tumor specimen sample) from a subject suffering from or suspected of being suffering from early stage colorectal cancer, determining the methylation level of an ID4 gene promoter, the expression level of an ID4 gene, or a combination thereof in the sample, and correlating the methylation level of the ID4 gene promoter, the expression level of the ID4 gene, or a combination thereof in the sample to a histopathological grade of the colorectal cancer.

The invention also provides a method of predicting the outcome of cancer, comprising obtaining a biological sample from a subject suffering from cancer, determining the methylation level of an ID4 gene promoter, the expression level of an ID4 gene, or a combination thereof in the sample, and correlating the methylation level of the ID4 gene promoter, the expression level of the ID4 gene, or a combination thereof in the sample to an outcome of the cancer.

The subject may suffer from or be at risk for developing American Joint Committee on Cancer stage I, II, III, or IV cancer. The sample may be a primary tumor sample. The outcome may be the survival of the subject after a surgical resection, e.g., a curative surgical resection. The cancer may be any type of cancer such as colorectal cancer, breast cancer, pancreatic cancer, or small bowel cancer.

The invention further provides a method of identifying a compound for treating colorectal cancer. The method comprises providing a colorectal cancer cell that contains an ID4 gene promoter, expresses an ID4 gene, or a combination thereof, contacting the cell with a test compound, and determining the methylation level of the ID4 gene promoter, the expression level of the ID4 gene, or a combination thereof in the cell. The methylation level of the ID4 gene promoter in the cell lower than a control methylation level, the expression level of the ID4 gene in the cell higher than a control expression level, or a combination thereof indicates that the test compound is a candidate for treating colorectal cancer.

Also within the invention is a method of treating colorectal cancer, comprising identifying a subject suffering from or at risk for developing colorectal cancer according to the method described above and administering to the subject an effective amount of a compound that decreases the methylation level of the ID4 gene promoter, increases the expression level of the ID4 gene, or a combination thereof in the subject.

In yet another aspect, the invention features a method of determining whether a subject having cancer is suffering from or at risk for developing metastasis (e.g., lymph node metastasis). The method comprises obtaining a biological sample from a subject having cancer and determining the methylation level of an ID4 gene promoter in the sample. The methylation level of the ID4 gene promoter in the sample higher than a control methylation level indicates that the subject is likely to be suffering from or at risk for developing metastasis.

The sample may be a benign lesion sample or an early stage primary tumor sample. The expression level of the ID4 gene in the sample may be lower than a control expression level. The cancer may be any type of cancer such as breast cancer, pancreatic cancer, colorectal cancer, or gastric cancer. In one embodiment, the sample is a T1, T2, or T3 breast cancer sample.

Furthermore, the invention provides a method of identifying a compound for treating breast cancer. The method comprises providing a breast cancer cell that contains an ID4 gene promoter, contacting the cell with a test compound, and determining the methylation level of the ID4 gene promoter in the cell. The methylation level of the ID4 gene promoter in the cell lower than a control methylation level indicates that the test compound is a candidate for treating breast cancer. In one embodiment, the cell is an early stage primary tumor cell.

Moreover, the invention provides a method of treating cancer. The method comprises identifying a subject having cancer and suffering from or at risk for developing lymph node metastasis according to the method described above and administering to the subject an effective amount of a compound that decreases the methylation level of the ID4 gene promoter, increases the expression level of the ID4 gene, or a combination thereof in the subject.

The invention also provides a method of treating breast cancer. The method comprises identifying a subject suffering from or at risk for developing breast cancer, wherein the methylation level of an ID4 gene promoter in the subject is higher than a control methylation value, and administering to the subject an effective amount of a compound that decreases the methylation level of the ID4 gene promoter, increases the expression level of the ID4 gene, or a combination thereof in the subject.

In the methods described above, the methylation level of the ID4 gene promoter may be determined by methylation-specific PCR, bisulfite sequencing, or a combination thereof. The expression level of the ID4 gene may be determined at the mRNA level, the protein level, or a combination thereof. The subject may be a human.

The above-mentioned and other features of this invention and the manner of obtaining and using them will become more apparent, and will be best understood, by reference to the following description, taken in conjunction with the accompanying drawings. These drawings depict only typical embodiments of the invention and do not therefore limit its scope.

DETAILED DESCRIPTION OF THE INVENTION

Figure 1:
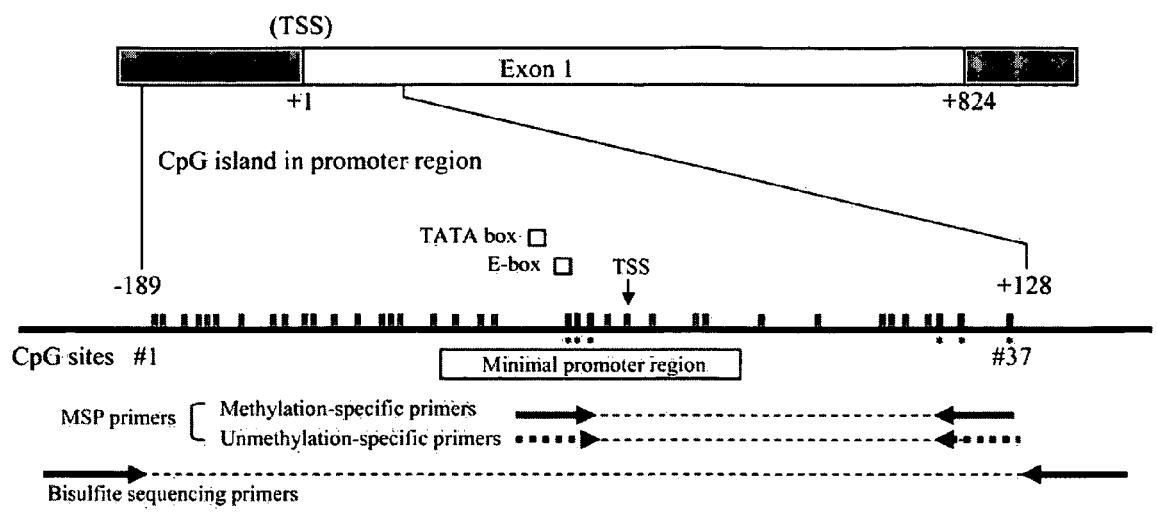
FIG. 1. Structure of the promoter region of ID4 gene and the primer design for methylation-specific PCR and bisulfite sequencing. CpG sites in the annealing site of methylation-specific PCR primers are indicated with "*". (TSS, transcription start site)

The invention is based at least in part upon the unexpected discovery that epigenetic inactivation of ID4 in colorectal carcinomas and breast correlates with poor differentiation and unfavorable prognosis and aberrant hypermethylation of ID4 gene promoter region increases risk of metastasis in colorectal and breast cancer.

More specifically, ID4 gene is a member of the inhibitor of DNA binding (ID) family proteins that inhibit DNA binding of basic helix-loop-helix transcription factors. The epigenetic inactivation of ID4 gene on colorectal cancer (CRC) development and its clinical significance was assessed.

In CRC cell lines, ID4 methylation status of the promoter region was assessed by methylation-specific PCR and bisulfite sequencing. The mRNA expression level was assessed by quantitative real-time reverse transcription-PCR. The methylation status of 9 normal epithelia, 13 adenomas (benign colorectal disease), 92 primary CRCs, and 26 liver metastases was assessed by methylation-specific PCR. ID4 protein expression was assessed by immunohistochemistry analysis of tissue specimen.

CRC cell lines were shown to be hypermethylated, and mRNA expression was suppressed and could be restored by 5-aza-cytidine treatment. In clinical specimens from normal epithelia, adenomas, primary CRCs, and liver metastases, the frequency of ID4 hypermethylation was 0 of 9 (0%), 0 of 13 (0%), 49 of 92 (53%), and 19 of 26 (73%), respectively, with a significant elevation according to CRC pathological progression. Methylation status of primary CRCs significantly correlated with histopathological tumor grade ($P=0.028$). Immunohistochemistry analysis showed ID4 expression of normal colon epithelia, adenomas, and unmethylated primary CRCs but not hypermethylated CRC specimens. Among 76 American Joint Committee on Cancer (AJCC) stage I to IV patients who had undergone curative surgical resection, overall survival was significantly poorer in patients with hypermethylated ID4 bearing tumors ($P=0.0066$).

Thus, ID4 gene is a potential tumor suppressor gene for which methylation status may play an important role in the CRC progression.

Furthermore, certain human primary breast cancers reportedly have low or no expression of ID4 protein, but its role in carcinogenesis and cancer progression is unknown. To determine its possible role, we examined epigenetic inactivation of ID4 gene by promoter hypermethylation in human breast cell lines and T1 breast cancer tissues. Methylation status of ID4 promoter CpG island was assessed by methylation-specific PCR (MSP); ID4 mRNA level was assessed by quantitative real-time RT-PCR. Of eight breast cancer cell lines, two were fully methylated, four were partially methylated, and two were not methylated. ID4 mRNA level was suppressed in fully methylated cell lines. ID4 hypermethylation was observed in 16 of 24 (67%) node-positive (stage III) and 7 of 36 (19%) node-negative T1 primary breast cancers matched by patient age and tumor diameter. It was a significant risk factor for nodal metastasis (OR 13.1, $P=0.0004$). ID4 mRNA level was suppressed in hypermethylated cancer specimens ($P=0.014$). Therefore, ID4 may play an important regulatory role in preventing tumor progression, and its silencing by hypermethylation may increases the risk of tumor progression and regional lymph node metastasis.

Accordingly, the invention provides various cancer diagnostic methods. One method is used to determine whether a subject is suffering from or at risk for developing colorectal cancer. In this method, a biological sample is obtained from a subject and the methylation level of an ID4 gene promoter, the expression level of an ID4 gene, or a combination thereof in the sample is determined. If the methylation level of the ID4 gene promoter in the sample is higher than a control methylation level, the expression level of the ID4 gene in the sample is lower than a control expression level, or a combination thereof, the subject is likely to be suffering from or at risk for developing colorectal cancer, e.g., primary or metastatic colorectal cancer. The control methylation level of the ID4 gene promoter and the control expression level of the ID4 gene may be, for example, the methylation level and the expression level detected in a normal epithelia sample or an adenomas sample.

Another method is used to determine whether a subject having cancer is suffering from or at risk for developing metastasis (e.g., lymph node metastasis). In this method, a biological sample (e.g., a benign lesion sample, an early stage primary tumor sample, or a T1, T2, or T3 breast cancer sample) is obtained from a subject having cancer (e.g., breast cancer, pancreatic cancer, colorectal cancer, or gastric cancer). The methylation level of an ID4 gene promoter in the sample is determined. If the methylation level of the ID4 gene promoter in the sample is higher than a control methylation level, the subject is likely to be suffering from or at risk for developing metastasis. In some embodiments, the expression level of the ID4 gene in the sample is lower than a control expression level. The control methylation level of the ID4 gene promoter may be, for example, the methylation level detected in a normal tissue sample, a primary tumor sample obtained from a subject without metastasis, or an isolated standard ID4 DNA.

"Subject," as used herein, refers to a human or animal, including all vertebrates, e.g., mammals, such as primates (particularly higher primates), sheep, dog, rodents (e.g., mouse or rat), guinea pig, goat, pig, cat, rabbit, cow; and non-mammals, such as chicken, amphibians, reptiles, etc. In a preferred embodiment, the subject is a human. In another embodiment, the subject is an experimental animal or animal suitable as a disease model.

A biological sample from a subject can be a tissue sample (e.g., a biopsy specimen sample, a normal or benign tissue sample, a freshly prepared tumor sample, a frozen tumor tissue sample, a paraffin-embedded tumor sample, a primary tumor sample, and a metastasis sample) or a body fluid sample (e.g., any body fluid in which cancer cells may be present, including, without limitation, blood, bone marrow, cerebral spinal fluid, peritoneal fluid, pleural fluid, lymph fluid, ascites, serous fluid, sputum, lacrimal fluid, stool, or urine). The tissues and body fluids can be collected using any of the methods well known in the art. Assessment of the paraffin-embedded specimen can be performed directly on a tissue section (5-12 microns thick) on the slide using bisulfite modification following extraction of DNA and MSP analysis.

An early stage tumor refers to a small tumor that has not invaded other tissues, i.e., no metastasis has occurred.

A "promoter" is a region of DNA extending 150-300 bp upstream from the transcription start site that contains binding sites for RNA polymerase and a number of proteins that regulate the rate of transcription of the adjacent gene. The promoter region of the ID4 gene is well known in the art. The minimal promoter region of ID4 is located at −48-+32.

Methods for extracting DNA from biological samples and determining the methylation level of a gene promoter are well known in the art. Commonly, DNA isolation procedures comprise lysis of cells using detergents. After cell lysis, proteins are removed from DNA using various proteases. DNA is then extracted with phenol, precipitated in alcohol, and dissolved in an aqueous solution.

The methylation level of a gene promoter can be determined, for example, by methylation-specific PCR, bisulfite sequencing (COBRA), or pyrosequencing.

A method for determining the methylation state of nucleic acids is described in U.S. Pat. No. 6,017,704 which is incorporated herein in its entirety. Methylation-specific PCR (MSR) is a technique whereby DNA is amplified by PCR dependent upon the methylation state of the DNA. Determining the methylation state of a nucleic acid includes amplifying the nucleic acid by means of oligonucleotide primers that distinguishes between methylated and unmethylated nucleic acids. MSP can rapidly assess the methylation status of virtually any group of CpG sites within a CpG island, independent of the use of methylation-sensitive restriction enzymes. This assay entails initial modification of DNA by sodium bisulfite, converting all unmethylated, but not methylated, cytosines to uracil, and subsequent amplification with primers specific for methylated versus unmethylated DNA. MSP requires only small quantities of DNA, is sensitive to 0.1% methylated alleles of a given CpG island locus, and can be performed on DNA extracted from paraffin-embedded samples. MSP eliminates the false positive results inherent to previous PCR-based approaches which relied on differential restriction enzyme cleavage to distinguish methylated from unmethylated DNA. This method is very simple and can be used on small amounts of tissue or few cells and fresh, frozen, or paraffin-embedded sections. MSP product can be detected by gel electrophoresis, capillary array electrophoresis, or real-time quantitative PCR.

Bisulfite sequencing is widely used to detect 5-methylcytosine (5-MeC) in DNA, and provides a reliable way of detecting any methylated cytosine at single-molecule resolution in any sequence context. The process of bisulfite treatment exploits the different sensitivity of cytosine and 5-MeC to deamination by bisulfite under acidic conditions, in which cytosine undergoes conversion to uracil while 5-MeC remains unreactive.

Gene expression can be detected and quantified at mRNA or protein level using a number of means well known in the art. To measure mRNA levels, cells in biological samples (e.g., cultured cells, tissues, and body fluids) can be lysed and the mRNA levels in the lysates or in RNA purified or semi-purified from the lysates determined by any of a variety of methods familiar to those in the art. Such methods include, without limitation, hybridization assays using detectably labeled gene-specific DNA or RNA probes and quantitative or semi-quantitative RT-PCR (e.g., real-time PCR) methodologies using appropriate gene-specific oligonucleotide primers. Alternatively, quantitative or semi-quantitative in situ hybridization assays can be carried out using, for example, unlysed tissues or cell suspensions, and detectably (e.g., fluorescently or enzyme-) labeled DNA or RNA probes. Additional methods for quantifying mRNA levels include RNA protection assay (RPA), cDNA and oligonucleotide microarrays, and colorimetric probe based assays.

Methods of measuring protein levels in biological samples are also known in the art. Many such methods employ antibodies (e.g., monoclonal or polyclonal antibodies) that bind specifically to target proteins. In such assays, an antibody itself or a secondary antibody that binds to it can be detectably labeled. Alternatively, the antibody can be conjugated with biotin, and detectably labeled avidin (a polypeptide that binds to biotin) can be used to detect the presence of the biotinylated antibody. Combinations of these approaches (including "multi-layer sandwich" assays) familiar to those in the art can be used to enhance the sensitivity of the methodologies. Some of these protein-measuring assays (e.g., ELISA or Western blot) can be applied to bodily fluids or to lysates of test cells, and others (e.g., immunohistological methods or fluorescence flow cytometry) applied to unlysed tissues or cell suspensions. Methods of measuring the amount of a label depend on the nature of the label and are known in the art. Appropriate labels include, without limitation, radionuclides (e.g., $^{125}$I, $^{131}$I, $^{35}$S, $^{3}$H, or $^{32}$P), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Other applicable assays include quantitative immunoprecipitation or complement fixation assays.

The invention also provides various cancer prognostic methods. One method is used to determine the histopathological grade of colorectal cancer. In this method, a biological sample (e.g., a benign or primary colorectal tumor specimen sample) is obtained from a subject suffering from or suspected of being suffering from early stage colorectal cancer. The methylation level of an ID4 gene promoter, the expression level of an ID4 gene, or a combination thereof in the sample is determined and correlated to a histopathological grade of the colorectal cancer.

Another method is used to predict the outcome of cancer. In this method, a biological sample (e.g., a primary tumor sample) is obtained from a subject suffering from cancer (e.g., colorectal cancer, breast cancer, pancreatic cancer, or small bowel cancer). The methylation level of an ID4 gene promoter, the expression level of an ID4 gene, or a combination thereof in the sample is determined and correlated to an outcome of the cancer. In one embodiment, the subject is suffering from or at risk for developing American Joint Committee on Cancer (AJCC) stage I, II, III, or IV cancer. In another embodiment, the outcome is the survival of the subject after a surgical resection, i.e., a noncurative or curative surgical resection.

The invention further provides methods for screening cancer treatment drugs. In one embodiment, the method is used to identify a compound for treating colorectal cancer. The method involves the steps of providing a colorectal cancer cell that contains an ID4 gene promoter, expresses an ID4 gene, or a combination thereof, contacting the cell with a test compound, and determining the methylation level of the ID4 gene promoter, the expression level of the ID4 gene, or a combination thereof in the cell. If the methylation level of the ID4 gene promoter in the cell is lower than a control methylation level, the expression level of the ID4 gene in the cell is higher than a control expression level, or a combination thereof, the test compound is identified as a candidate for treating colorectal cancer. The control methylation level and the control expression level may be, for example, the methylation level and the expression level detected in the colorectal cancer cell prior to the contacting step.

In another embodiment, the method is used to identify a compound for treating breast cancer. The method involves the steps of providing a breast cancer cell (e.g., an early stage primary tumor cell) that contains an ID4 gene promoter, contacting the cell with a test compound, and determining the methylation level of the ID4 gene promoter in the cell. If the methylation level of the ID4 gene promoter in the cell is lower than a control methylation level, the test compound is identified as a candidate for treating breast cancer. The control methylation level may be, for example, the methylation level detected in the breast cancer cell prior to the contacting step.

The test compounds of the present invention can be obtained using any of the numerous approaches (e.g., combinatorial library methods) known in the art. See, e.g., U.S. Pat. No. 6,462,187. Such libraries include, without limitation, peptide libraries, peptoid libraries (libraries of molecules having the functionalities of peptides, but with a novel, non-peptide backbone that is resistant to enzymatic degradation), spatially addressable parallel solid phase or solution phase libraries, synthetic libraries obtained by deconvolution or affinity chromatography selection, and the "one-bead one-compound" libraries. Compounds in the last three libraries can be peptides, non-peptide oligomers, or small molecules. Examples of methods for synthesizing molecular libraries can be found in the art. Libraries of compounds may be presented in solution, or on beads, chips, bacteria, spores, plasmids, or phages.

To identify a compound for treating cancer, a cancer cell or a subject that contains an ID4 gene promoter, expresses an ID4 gene, or a combination thereof is provided. The cell or subject may be a cell or subject that naturally contains an ID4 gene promoter, expresses an ID4 gene, or a combination thereof, or alternatively, a cell or subject that contains a recombinant form of an ID4 gene promoter, expresses a recombinant form of an ID4 gene, or a combination thereof.

The compounds of the invention can be incorporated into pharmaceutical compositions. Such compositions typically include the compounds and pharmaceutically acceptable carriers. "Pharmaceutically acceptable carriers" include solvents, dispersion media, coatings, antibacterial and antifungal agents, isotonic and absorption delaying agents, and the like, compatible with pharmaceutical administration. Other active compounds (e.g., taxol, doxorubicin, or 5-FU) can also be incorporated into the compositions.

A pharmaceutical composition is formulated to be compatible with its intended route of administration. See, e.g., U.S. Pat. No. 6,756,196. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In one embodiment, the compounds are prepared with carriers that will protect the compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens)

can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. "Dosage unit form," as used herein, refers to physically discrete units suited as unitary dosages for the subject to be treated; each unit containing a predetermined quantity of active compound calculated to produce the desired therapeutic effect in association with the required pharmaceutical carrier.

In addition, the invention provides methods for treating cancer. In one embodiment, the method is used to treat colorectal cancer. The method involves the steps of identifying a subject suffering from or at risk for developing colorectal cancer according to the method described above and administering to the subject an effective amount of a compound that decreases the methylation level of the ID4 gene promoter, increases the expression level of the ID4 gene, or a combination thereof in the subject.

In another embodiment, the method is used to treat cancer. The method involves the steps of identifying a subject having cancer and suffering from or at risk for developing lymph node metastasis according to the method described above and administering to the subject an effective amount of a compound that decreases the methylation level of the ID4 gene promoter, increases the expression level of the ID4 gene, or a combination thereof in the subject.

In still another embodiment, the method is used to treat breast cancer. A subject suffering from or at risk for developing breast cancer is identified where the methylation level of an ID4 gene promoter in the subject is higher than a control methylation value. An effective amount of a compound is administered to the subject to decrease the methylation level of the ID4 gene promoter, increase the expression level of the ID4 gene, or a combination thereof in the subject. The control methylation level may be, for example, the methylation level detected in a normal tissue sample.

The term "treating" is defined as administration of a substance to a subject with the purpose to cure, alleviate, relieve, remedy, prevent, or ameliorate a disorder, symptoms of the disorder, a disease state secondary to the disorder, or predisposition toward the disorder. A subject to be treated may be identified, e.g., using the diagnostic methods described above.

An "effective amount" is an amount of a compound that is capable of producing a medically desirable result in a treated subject. The medically desirable result may be objective (i.e., measurable by some test or marker) or subjective (i.e., subject gives an indication of or feels an effect). The treatment methods can be performed alone or in conjunction with other drugs and/or radiotherapy. See, e.g., U.S. Patent Application 20040224363.

In one in vivo approach, a therapeutic compound (e.g., a compound that decreases the methylation level of an ID4 gene promoter, increases the expression level of an ID4 gene, or a combination thereof in a subject) itself is administered to a subject. For example, the therapeutic compound may be an ID4 protein or a nucleic acid encoding an ID4 protein. The therapeutic compound can be a demethylating agent such as 5-aza-cytidine or a compound capable of demethylating CpG islands methylated in promoter regions. These compounds can reverse gene silencing and activate gene expression. Other types of compounds are histone deacetylase (HDAC) inhibitors such as Trichostatin which can modify histones in chromatin regions and activate genes silenced by methylation of CpG islands in promoter regions. There are HDAC inhibitors available for in vitro and clinical trials.

Generally, the compound will be suspended in a pharmaceutically-acceptable carrier and administered orally, or by intravenous (i.v.) infusion, or injected or implanted subcutaneously, intramuscularly, intrathecally, intraperitoneally, intrarectally, intravaginally, intranasally, intragastrically, intratracheally, or intrapulmonarily. For treatment of cancer, the compound is preferably delivered directly to tumor cells, e.g., to a tumor or a tumor bed following surgical excision of the tumor, in order to kill any remaining tumor cells. For prevention of cancer invasion and metastases, the compound can be administered to, for example, a subject that has not yet developed detectable invasion and metastases but is found to have increased methylation level of an ID4 gene promoter, decreased expression level of an ID4 gene, or a combination thereof. The dosage required depends on the choice of the route of administration, the nature of the formulation, the nature of the subject's illness, the subject's size, weight, surface area, age, and sex, other drugs being administered, and the judgment of the attending physician. Suitable dosages are in the range of 0.01-100.0 mg/kg. Wide variations in the needed dosage are to be expected in view of the variety of compounds available and the different efficiencies of various routes of administration. For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

In some embodiments, polynucleotides are administered to a subject. Polynucleotides can be delivered to target cells by, for example, the use of polymeric, biodegradable microparticle or microcapsule devices known in the art. Another way to achieve uptake of the nucleic acid is using liposomes, prepared by standard methods. The polynucleotides can be incorporated alone into these delivery vehicles or co-incorporated with tissue-specific or tumor-specific antibodies. Alternatively, one can prepare a molecular conjugate composed of a polynucleotide attached to poly-L-lysine by electrostatic or covalent forces. Poly-L-lysine binds to a ligand that can bind to a receptor on target cells. "Naked DNA" (i.e., without a delivery vehicle) can also be delivered to an intramuscular, intradermal, or subcutaneous site. A preferred dosage for administration of polynucleotide is from approximately $10^6$ to $10^{12}$ copies of the polynucleotide molecule.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLE I

Epigenetic Inactivation of Id4 in Colorectal Carcinomas Correlates with Poor Differentiation and Unfavorable Prognosis We hypothesized that ID4 gene may be expressed in normal colon epithelium and have a putative tumor suppressive role in CRC, contrary to other ID members. To examine this hypothesis, we assessed the methylation status of CRCs. We found that ID4 gene transcription is silenced during CRC development and that hypermethylation of the ID4 promoter region is one of the main mechanisms of inactivation.

Materials and Methods

Cell Lines. Three CRC cell lines SW480, DLD1, and LOVO (American Type Culture Collection, Manassas, Va.) were analyzed in this study. Genomic DNA was extracted from cells as described previously (33). Total RNA was extracted with TRI Reagent (Molecular Research Center, Inc., Cincinnati, Ohio) according to the manufacturer's protocol. For ID4 expression restoration study, SW480 and DLD1 were treated with DNA demethylation agent 5-azacytidine (5Aza), a known inhibitor of methylation, as described previously (33-35). Cells were seeded at $7\times10^5$/T-25 flask on day zero; the culture medium was changed on day two, and cells were then treated with 5Aza at final concentrations of 5 ug/mL for 48 hours (SW480 and DLD1) and 10 ug/mL for 72 hours (DLD1). After treatment, cells were harvested for DNA and RNA as described above.

Tissue Specimens and Clinicopathological Information. For the analysis of methylation status at ID4 promoter region, we studied 131 colorectal tumors (13 adenomas, 92 primary CRCs, and 26 liver metastases) from 122 patients randomly selected by the database coordinator from those who underwent colectomy or proctectomy between 1996 and 2001 at Saint John's Health Center (Santa Monica, Calif.). Nine normal colorectal epithelial tissues were obtained simultaneously from patients with primary CRC. All patients in this study were consented according to the guidelines set forth by JWCI Institutional Review Board committee. Tumors were classified and staged according to the revised guidelines set by the American Joint Committee on Cancer (36). Clinicopathological data from the tumor registry were obtained after Institutional Review Board approval for all of the patients.

DNA Extraction from Tissue Specimens and Bisulfite Modification. Several 5-um sections were cut with a microtome from formalin-fixed, paraffin-embedded blocks under sterile conditions as described previously (37). One section for each tumor was stained with hematoxylin after deparaffinization, and the tumor tissues were precisely microdissected under a microscope. Dissected tissues were digested with 50 uL of proteinase K containing lysis buffer at 50° C. for 5 hours, followed by heat deactivation of proteinase K at 95° C. for 10 minutes.

Sodium bisulfite modification was applied on extracted genomic DNA of tissue specimens or cell lines for methylation-specific PCR or bisulfite sequencing as described previously (33).

Detection of Hypermethylation. Methylation status of ID4 promoter region was analyzed by methylation-specific PCR and bisulfite sequencing. Because the "minimal promoter region" (−48 to +32) of ID4 gene had been shown previously by deletion analysis for promoter determination (38), we were able to design highly specific methylation-specific PCR primer sets (FIG. 1). Forward primers for methylation-specific PCR covered the TATA box, E-box, and three CpG sites in the ID4 minimal promoter region; reverse primers covered three CpG sites. The methylation-specific primer set was as follows: forward, 5'-D4-TTTTATAAATATAGT-TGCGCGGC-3'; and reverse, 5'-GAAACTCCGACTAAAC-CCGAT-3'. The unmethylation-specific primer set was as follows: forward, 5'-D3-TTTTATAAATATAGTTGTGTGGTGG-3'; and reverse, 5'-TCAAAACTCCAACTAAACCCAAT-3'. PCR amplification was done in a 10-uL reaction volume with 1 uL template for 40 cycles of 30 seconds at 94° C., 30 seconds at 58° C., and 30 seconds at 72° C., followed by a 7-minute final extension at 72° C. $Mg^{2+}$ concentration was 1.5 mmol/L for methylation-specific primer set and 2.5 mmol/L for unmethylation-specific primer set. Primer concentration was 0.1 mmol/L for methylation-specific primer set and 0.4 mmol/L for unmethylation-specific primer set. PCR products were detected and analyzed by CEQ 8000XL capillary array electrophoresis system (Beckman Coulter, Inc., Fullerton, Calif.) with CEQ 8000 software version 6.0 (Beckman Coulter) as described previously (35). Methylation status was determined by the ratio of the signal intensities of methylated and unmethylated PCR products; samples with methylated to unmethylated ratio larger than 0.2 were determined as methylated. Each primer set was confirmed not to yield amplification on DNA without bisulfite treatment.

For bisulfite sequencing, the primer set was as follows: forward, 5'-TTTTATTYGGGTAGTYGGATTTT-TYGTTTTTTAGTAT-3'; and reverse, 5'-CCCAC-CCRAATATCCTAATCACTCCCTTC-3', with Y=C or T, R=G or A, as described previously (32). PCR amplification was done in a 50-uL reaction volume with 2 uL template for 40 cycles of 30 seconds at 94° C., 30 seconds at 60° C., and 30 seconds at 72° C., followed by a 7-minute final extension at 72° C. with the use of 2.5 mmol/L of $Mg^{2+}$. Purified PCR products were directly sequenced with CEQ DYE Terminator Cycle Sequencing kit (Beckman Coulter, Inc.). Cycling program includes 30 cycles of 20 seconds at 95° C., 40 seconds at 55° C., and 4 minutes at 60° C. Sequences were read by CEQ 8000XL capillary array electrophoresis system (Beckman Coulter) with CEQ 8000 software version 6.0 (Beckman Coulter) as described previously (37).

Analysis of mRNA Expression Level. Reverse-transcriptase reactions were done on 1.0 ug of extracted total RNA with Moloney murine leukemia virus reverse-transcriptase (Promega, Madison, Wis.) with oligodeoxythymidylic acid primers, as described previously (39). Quantitative real-time reverse transcription-PCR assay was done on the iCycler iQ Real-Time thermocycler detection system (Bio-Rad Laboratories, Hercules, Calif.; 39). For each PCR, the reaction mixture consisted of cDNA template synthesized by reverse-transcription from 250 ng of total RNA, 0.2 mmol/L of forward primer (5'-CGCTCACTGCGCT-CAACAC-3'), 0.2 mmol/L of reverse primer (5'-TCAGGCG-GCCGCACACCT-3'), and 0.6 mmol/L of fluorescence resonance energy transfer probe (5'-FAM-CATTCTGTGCCGCTGAGCCG-BHQ-3'). PCR amplification was done in a 20-ul reaction volume for 45 cycles of 30 seconds at 94° C., 30 seconds at 58° C., and 30 seconds at 72° C. with 3 mmol/L of $Mg^{2+}$. Absolute copy numbers were determined by a standard curve with serial dilutions ($10^8$ to $10^1$ copies) of DNA containing ID4 or GAPDH cDNA sequence. Analysis without templates was done as a negative control in each study. PCR products were electrophoresed on 2% agarose gels to confirm correct product size and absence of nonspecific bands. The expression level of the housekeeping gene GAPDH was measured as an internal reference with a standard curve to determine the integrity of template RNA for all of the specimens. The ratio of ID4 and GAPDH mRNA level was calculated as follows: (absolute copy number of ID4)/(absolute copy number of GAPDH) as described previously (39).

Immunohistochemistry. Immunohistochemistry analysis of ID4 protein expression in primary CRCs, adenomas, and normal colon tissue sections was done to determine concordance with methylation-specific PCR results. Immunohistochemistry was done on 3-um sections of formalin-fixed, paraffin-embedded tissues, which were placed on silanecoated slides and baked at 60° C. for 1 hour. Afterward, the slides were deparaffinized, hydrated, and placed in antigen retrieval buffer (DAKO Corporation, Carpinteria, Calif.) at 95° C. for 10 minutes. Endogenous peroxidase activity was quenched by 1% hydrogen peroxide for 10 minutes. After blocking with 1% BSA for 60 minutes, 1:100 dilution of an anti-ID4 polyclonal rabbit IgG antibody, sc-491 (Santa Cruz Biotechnology, Inc., Santa Cruz, Calif.), was applied and incubated for 3 hours at room temperature. After washing in PBS, antibody binding was visualized with DAKO LSAB+kit (DAKO Corporation) followed by diaminobenzidine staining with DAB substrate kit for peroxidase (Vector Laboratories, Inc., Burlingame, Calif.) for 2 minutes at room temperature. The sections were lightly counterstained with hematoxylin and then mounted. As negative controls, adjacent sections of each ID4 immunostained section were stained simultaneously without primary antibody.

showed mixture of methylation and unmethylation. For a negative control, DNA from peripheral blood lymphocytes obtained from a healthy donor, which was determined to be unmethylated by methylation-specific PCR, was assessed by bisulfite sequencing. All sequenced CpG sites were unmethylated in peripheral blood lymphocytes (FIG. 2A). It was verified that methylation-specific PCR results represent the methylation status of promoter region accurately in our assays.

To assess the mRNA expression level of ID4, we did quantitative real-time reverse transcription-PCR. In the SW480 and DLD1 cell lines, ID4 mRNA expression was not detected. In contrast, the partially hypermethylated LOVO cell line had $1.4 \times 10^5$ copies/250 ng of total RNA, and the ID4 to GAPDH expression ratio was $2.5 \times 10^{-2}$ (Table 1).

TABLE I

| | ID4 mRNA expression level of CRC cell lines | | | | |
|---|---|---|---|---|---|
| | SW480 | SW480 (5Aza*) | DLD1 | DLD1 (5Aza*) | LOVO |
| ID4 copy number † | 0 | $4.7 \times 10^2$ | 0 | $4.8 \times 10^2$ | $1.4 \times 10^5$ |
| GAPDH copy number † | $4.6 \times 10^6$ | $1.7 \times 10^5$ | $5.6 \times 10^5$ | $9.9 \times 10^4$ | $5.5 \times 10^6$ |
| ID4 expression ratio ‡ | 0 | $2.8 \times 10^{-3}$ | 0 | $4.8 \times 10^{-3}$ | $2.5 \times 10^{-2}$ |

*5Aza: Cell lines were treated with 5Aza-cytidine.
† Absolute copy number per 250 ng of total RNA.
‡ Calculated as (ID4 copy number)/(GAPDH copy number).

Statistical Analysis. The relation between methylation status of ID4 gene promoter region and tumor classification was assessed with Fisher's exact test, $x^2$ test, and Cochran-Armitage trend test. The relation between ID4 methylation and clinicopathological characteristics was assessed with Fisher's exact test, $x^2$ test, and Wilcoxon's rank-sum test for univariate analysis and logistic regression model for multivariate analysis. For survival analysis grouping with ID4 methylation, Kaplan-Meier analysis was used, and differences between the survival curves were analyzed with the log-rank test. Cox's proportional hazard regression models were used for univariate and multivariate analyses of clinicopathological characteristics and prognosis. Variables suggested by the univariate analyses (P<0.10), except for the highly dependent variable of ID4 methylation, were entered into the multivariate analyses. The statistical package SAS JMP version 5.0.1 (SAS Institute Inc., Cary, N.C.) was used to conduct statistical analyses. A P<0.05 (two-tailed) was considered as significant.

Results

Figure 2:
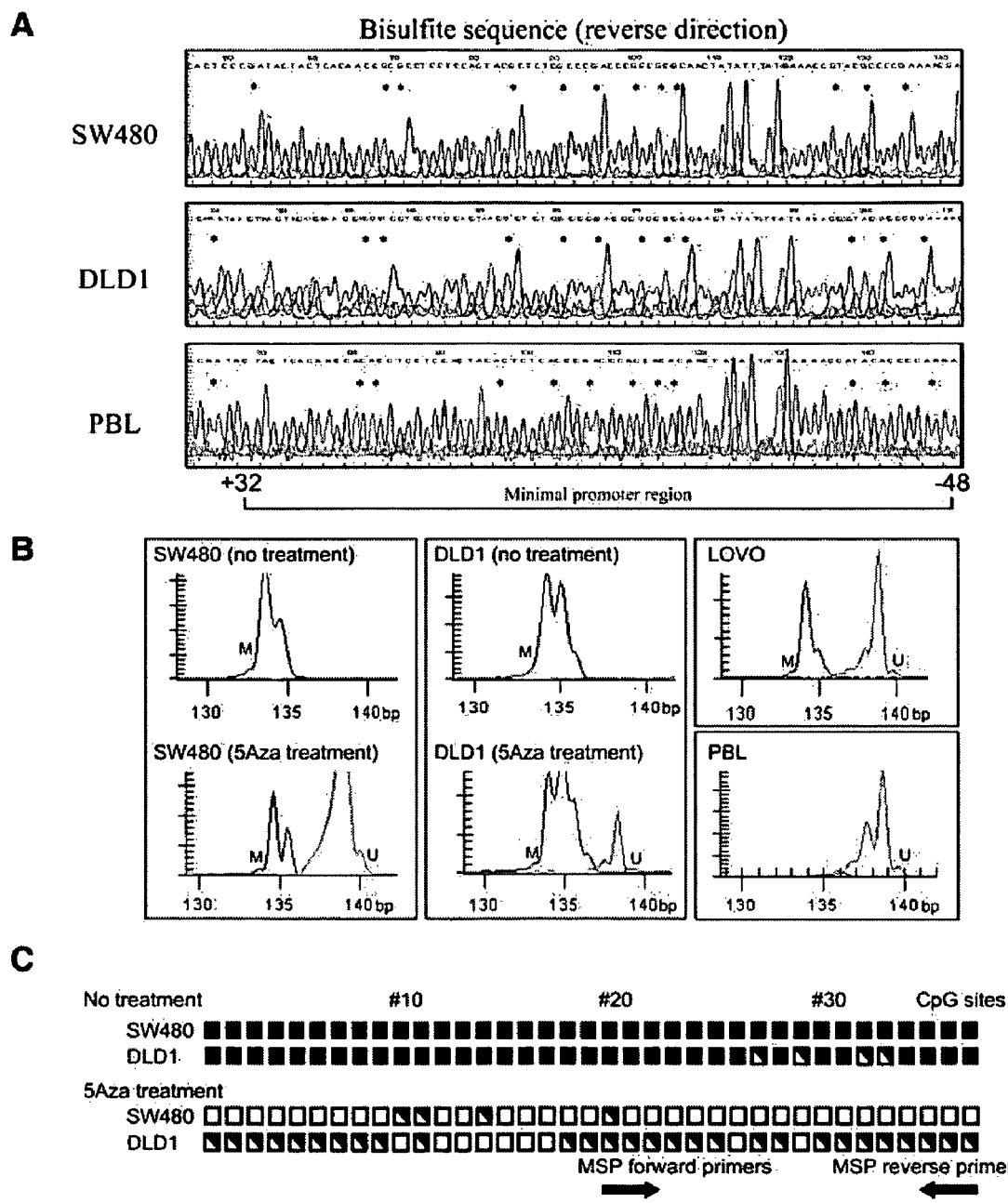
FIG. 2. A. Representative bisulfite sequencing (reverse direction) of CRC (colorectal cancer) established cell lines (SW480 and DLD1) and peripheral blood lymphocytes in relation to the minimal promoter region. CpG sites (*) were fully methylated in SW480, mostly methylated in DLD1, and not methylated in peripheral blood lymphocytes. These findings corresponded to the methylation-specific PCR results. B. Methylation-specific PCR results of CRC cell lines (SW480, DLD1, and LOVO), peripheral blood lymphocytes, and 5Aza-treated cell lines (SW480 and DLD1). M: methylation-specific product of methylation-specific PCR; U: unmethylation-specific product of methylation-specific PCR. In SW480 and DLD1, only methylated peaks were observed. In LOVO, both methylated and unmethylated peaks were observed. Unmethylated peaks appeared in SW480 and DLD1 after 5Aza treatment. C. Methylation status of each CpG site read by bisulfite sequencing of nontreated and 5Aza-treated SW480 and DLD1. ■, methylated CpG; ◨ partially methylated or heterozygously methylated CpG; and □, unmethylated CpG. (PBL, peripheral blood lymphocytes)

Cell Line Analysis. Among the three CRC cell lines studied, SW480 and DLD1 showed only methylation-specific peaks by methylation-specific PCR and were determined as hypermethylated, and LOVO showed both methylation-specific and unmethylation-specific peaks by methylation-specific PCR and was determined as hypermethylated (FIG. 2B). Because methylation-specific PCR results depend on the methylation status of only six CpG sites at the primer annealing sites, we did bisulfite sequencing of the promoter region. All of the sequenced CpG sites were methylated in SW480 and most of them were methylated in DLD1 (FIG. 2). In LOVO, sequence results at about one-third of CpG sites To ascertain that ID4 transcription down-regulation was caused by promoter hypermethylation, hypermethylated cell lines were treated with the DNA demethylating agent 5Aza. After treatment with 5 ug/mL of 5Aza for 48 hours, SW480 showed an unmethylation-specific peak by methylation-specific PCR analysis (FIG. 2B). Bisulfite sequencing revealed that most CpG sites were changed to unmethylated form (FIG. 2C), whereas all of the CpG sites of nontreated cells remained methylated. ID4 expression was restored from an undetectable level to $4.7 \times 10^2$ copies/250 ng of total RNA (Table 1). Because the treatment with 5 ug/mL of 5Aza for 48 hours did not overtly restore ID4 expression in DLD1, the dose and duration of exposure were increased to 10 ug/mL of 5Aza for 72 hours. This treatment produced an unmethylation-specific peak on methylation-specific PCR analysis (FIG. 2B), and bisulfite sequencing revealed that CpG sites partially lost their methylation (FIG. 2C). ID4 expression was restored from an undetectable level to $4.8 \times 10^2$ copies/250 ng of total RNA (Table 1).

Tumor Progression of Clinical Specimens and ID4 Methylation Status. To show the changes in ID4 methylation status during CRC development, we assessed each stage of CRC progression. ID4 hypermethylation was not detected in nine normal colon epithelia or in 13 adenomas, but it was identified in 49 of 92 (53%) primary CRCs and in 19 of 26 (73%) liver metastases. The frequency of hypermethylation was significantly higher in primary carcinomas than in adenomas (P=0.0002 by Fisher's exact test). In addition, the frequency of hypermethylation was significantly increased as the tumor progressed from adenoma to primary carcinoma and then to metastatic CRC(P<0.0001 by $x^2$ test; P<0.0001 by Cochran-Armitage trend test; Table 2).

TABLE 2

ID4 hypermethylation and tumor type

| Tumor type | No. of tumors (% of total) | | P |
|---|---|---|---|
| | Methylated | Unmethylated | |
| Adenomas | 0 (0) | 13 (100) | 0.0002* |
| Primary carcinomas | 49 (53) | 43 (47) | <0.0001† |
| Liver metastases | 19 (73) | 7 (27) | |

*Fisher's exact test (adenomas versus primary carcinomas).
†$\chi^2$ test and Cochran-Armitage trend test.

Figure 3:
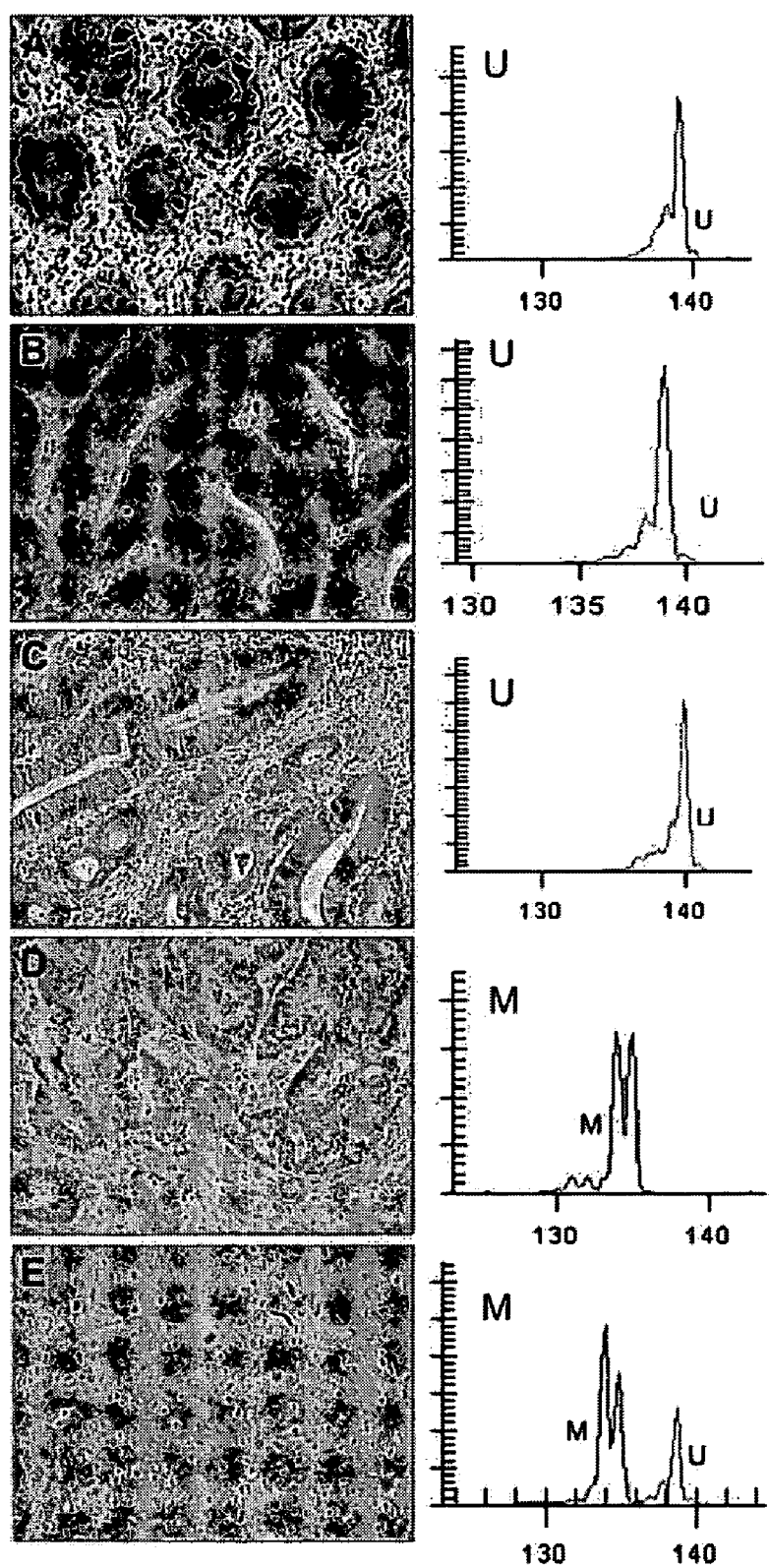
FIG. 3. Representative immunohistochemistry of primary CRCs and normal colonic epithelium with their respective methylation-specific PCR results. The vertical axes of methylation-specific PCR results are the fluorescent intensity representing the amount of PCR amplicon. A, normal colonic epithelium. Diffusely stained cytoplasm represents high concentration of ID4 protein. B, adenoma. All adenomas were unmethylated. Lightly stained cytoplasm represents ID4 protein. C, primary CRC determined as unmethylated by methylation-specific PCR. Lightly stained cytoplasm represents ID4 protein. This tumor was well to moderately differentiated carcinoma. D and E, primary CRCs determined as methylated by methylation-specific PCR. Cytoplasm is not stained. D and E tumors were poorly differentiated carcinoma and mucinous carcinoma, respectively. (U, unmethylated; M, methylated)

Immunohistochemistry. Of the 10 primary CRCs analyzed with immunohistochemistry, six were hypermethylated and four were unmethylated. In FIG. 3, representative immunohistochemistry results are aligned with corresponding methylation-specific PCR results. Normal colonic epithelia and adenomas had diffusely stained cytoplasm, representing high concentration of ID4 protein expression (FIGS. 3, A and B). In primary CRCs determined as unmethylated by methylation-specific PCR, cell cytoplasm was lightly stained for ID4 protein. A representative microscopic picture of an unmethylated primary CRC, which was well to moderately differentiated carcinoma, is shown in FIG. 3C. In contrast, cytoplasm of primary CRCs determined as hypermethylated by methylation-specific PCR did not immunostain. Representative microscopic pictures of hypermethylated primary CRCs, which were poorly differentiated carcinoma and mucinous carcinoma, are shown in FIG. 3, D and E, respectively. No nuclear staining was observed in any type of tissues.

Clinical Analysis. Methylation status of primary CRCs was independent of sex, age, tumor location, tumor diameter, American Joint Committee on Cancer tumor-node-metastasis (TNM) scores, and stage (Table 3). However, there was a significant correlation with histopathological tumor grade, which represents tumor cell differentiation (P=0.028, Fisher's exact test). In a multivariate analysis of hypermethylation status by logistic regression model, histopathological tumor grade and TNM T score were incorporated by stepwise variable selection, but only the histopathological tumor grade was significant for methylation status (P=0.025).

TABLE 3

ID4 hypermethylation and clinicopathological characteristics of primary CRC (n = 92)

| Variable | No. of patients (% of total) | | P |
|---|---|---|---|
| | Methylated | Unmethylated | |
| Total no. of patients | 49 (53) | 43 (47) | |
| Sex | | | 0.53* |
| male | 21 (49) | 22 (51) | |
| female | 28 (57) | 21 (43) | |
| Age (yr) median | 74 | 73 | 0.51† |
| youngest | 39 | 40 | |
| oldest | 94 | 94 | |
| Tumor site | | | 0.41* |
| right colon | 24 (59) | 17 (41) | |
| left colon/rectum | 25 (49) | 26 (51) | |
| Tumor diameter (mm) median | 50 | 45 | 0.27† |
| minimum | 9 | 18 | |
| maximum | 125 | 95 | |
| AJCC primary tumor (T) | | | 0.28‡ |
| T1 | 6 (86) | 1 (14) | |
| T2 | 5 (50) | 5 (50) | |
| T3 | 29 (49) | 30 (51) | |
| T4 | 9 (56) | 7 (44) | |
| AJCC regional lymph nodes (N) | | | 0.39‡ |
| N0 | 24 (52) | 22 (48) | |
| N1 | 13 (46) | 15 (54) | |
| N2 | 12 (67) | 6 (33) | |
| AJCC distant metastasis (M) | | | 0.18* |
| M0 | 36 (52) | 33 (48) | |
| M1 | 13 (57) | 10 (43) | |
| AJCC stage | | | 0.15‡ |
| I | 11 (79) | 3 (21) | |
| II | 11 (42) | 15 (58) | |
| III | 15 (50) | 15 (50) | |
| IV | 12 (55) | 10 (45) | |
| Histopathological grade | | | 0.028* |
| well/moderate | 28 (44) | 34 (56) | |
| poor/undifferentiated | 21 (74) | 9 (26) | |

*Fisher's exact test.
†Wilcoxon's rank-sum test.
‡$\chi^2$ test.

Of the 92 patients from whom primary CRC tissue was obtained, 16 underwent noncurative resection; all of these patients had American Joint Committee on Cancer stage 1V disease with irresectable remote metastases or local invasion. Four of the 16 patients expired from surgery-related causes within 30 postoperative days and were therefore excluded from survival analysis; the remaining 12 had primary CRCs that were hypermethylated (n=7) or unmethylated (n=5). Table 4 shows the results of univariate survival analysis for the 88 evaluable patients and for the subgroup of 76 patients who underwent curative surgical resection of CRC. Methylation status, TNM stage, N score, methylated score, histopathological tumor grade, and tumor diameter were significantly correlated with survival in both groups by Cox's regression analysis.

TABLE 4

Univariate analysis of overall survival of stage I–IV patients according to risk factors

| Variable | Evaluable patients* (n = 88) | | Patients who underwent curative surgical resections† (n = 76) | |
|---|---|---|---|---|
| | Relative risk (95% CI) | P‡ | Relative risk (95% CI) | P‡ |
| Age | 1.01 (0.98, 1.04) | 0.50 | 1.01 (0.98, 1.06) | 0.45 |
| Tumor site | | 0.24 | | 0.79 |
| [left/rectum] | 0.81 (0.57, 1.15) | | 0.94 (0.61, 1.49) | |
| Tumor diameter | 1.02 (1.00, 1.03) | 0.025 | 1.02 (1.00, 1.04) | 0.015 |

TABLE 4-continued

Univariate analysis of overall survival of stage I–IV patients according to risk factors

| Variable | Evaluable patients* (n = 88) | | Patients who underwent curative surgical resections† (n = 76) | |
|---|---|---|---|---|
| | Relative risk (95% CI) | P‡ | Relative risk (95% CI) | P‡ |
| AJCC primary tumor (T) | | 0.080 | | 0.61 |
| [T2-T1] | 1.35 (0.13, 29.0) | | 1.33 (0.13, 28.5) | |
| [T3-T2] | 2.40 (0.70, 15.0) | | 1.67 (0.46, 10.7) | |
| [T4-T3] | 1.81 (0.78, 3.86) | | 1.43 (0.40, 4.05) | |
| AJCC regional lymph nodes (N) | | 0.0018 | | 0.010 |
| [N1-N0] | 2.01 (0.83, 4.91) | | 2.42 (0.80, 7.53) | |
| [N2-N1] | 2.36 (1.02, 5.61) | | 2.28 (0.77, 6.65) | |
| AJCC distant metastasis (M) | | <0.0001 | | 0.019 |
| [M1-M0] | 8.49 (4.13, 17.6) | | 4.01 (1.30, 10.4) | |
| AJCC stage | | <0.0001 | | 0.08 |
| [II-I] | 1.21 (0.24, 8.75) | | 1.22 (0.24, 8.79) | |
| [III-II] | 2.42 (0.81, 8.81) | | 2.41 (0.81, 8.79) | |
| [IV-III] | 4.74 (2.14, 11.0) | | 1.94 (0.53, 5.82) | |
| Histopathological grade | | 0.011 | | 0.017 |
| [poor/undifferentiated] | 1.59 (1.12, 2.25) | | 1.73 (1.11, 2.71) | |
| ID4 methylation status | | 0.017 | | 0.0049 |
| [methylated] | 1.56 (1.08, 2.36) | | 2.02 (1.22, 3.77) | |

Abbreviation:
CI. confidence interval.
*Evaluable patients with AJCC satge I–IV primary CRC, including 12 patients who underwent noncurative resections.
†Subgroup of evaluable patients.
‡By Cox's proportional hazard model.

Figure 4:
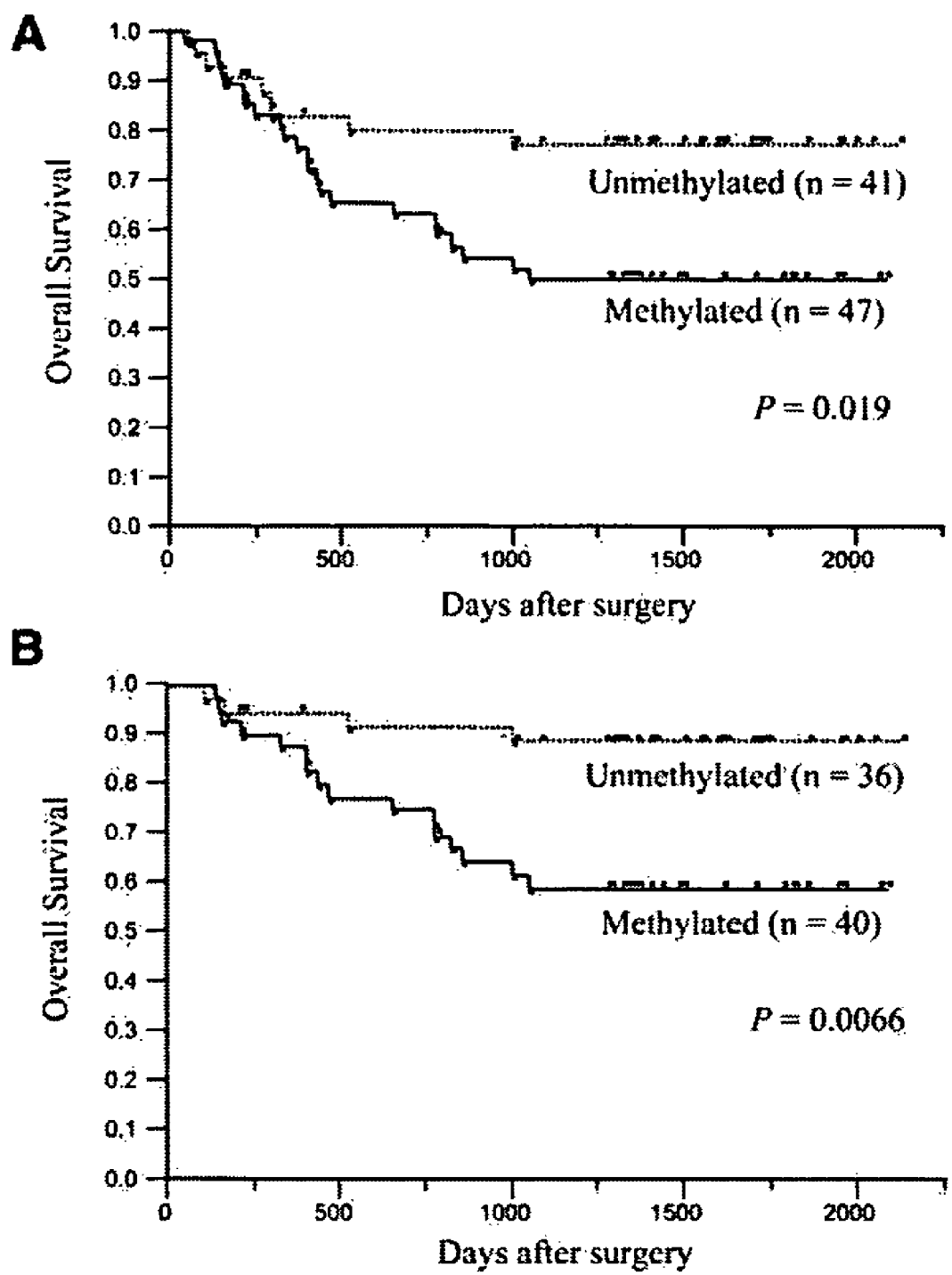
FIG. 4. Kaplan-Meier analysis of overall survival for CRC patients whose primary tumors were assessed for methylation status of ID4 promoter region. A. Among the 88 evaluable patients, these with methylated primary tumors had a significantly ($P=0.019$) worse prognosis. B. Among the subgroup of the 76 patients who underwent curative surgical resection of CRC, these with methylated primary tumors had a significantly ($P=0.0066$) worse prognosis. (n, number of patients)

Among the 88 evaluable patients, those whose primary CRC was unmethylated had significantly better prognosis by Kaplan-Meier analysis (P=0.019, log-rank test; FIG. 4A). This difference was even more significant in the 76 patients who underwent curative surgical resection (P=0.0066, log-rank test; FIG. 4B): 5-year survival rates were 88% and 59% in unmethylated and methylated groups, respectively.

In a multivariate analysis of Cox's proportional hazard model, methylation status, TNM N and methylated score, and tumor diameter were selected as covariates that had P values under 0.1 in univariate analysis. TNM stage was not selected because of the direct association with the TNM N and methylated score, and histopathological tumor grade was not selected because it was highly dependent on ID4 methylation status. The risk ratio of ID4 hypermethylation was 1.82 (95% confidence interval 1.09-3.43; P=0.020; Table 5). Hypermethylation of the ID4 promoter region was identified as an independent prognostic factor.

TABLE 5

Multivariate analysis of overall survival of patients who underwent curative surgical resections (n = 76)

| Covariate | Relative risk (95% CI) | P* |
|---|---|---|
| Tumor diameter | 1.02 (1.00, 1.04) | 0.11 |
| AJCC Regional lymph nodes (N) | | 0.17 |
| [N1-N0] | 1.87 (0.58, 6.16) | |
| [N2-N1] | 2.65 (0.80, 7.58) | |
| AJCC Distant metastasis (M) | | |
| [M1-M0] | 2.65 (0.80, 7.58) | 0.10 |
| ID4 methylation status | | 0.020 |
| [methylated] | 1.82 (1.09, 3.43) | |

*By Cox's proportional hazard model.

SUMMARY

This is the first report of ID4 inactivation in CRC and its effect on overall survival. Because ID4 is suggested as one of the key controlling factors for cell differentiation, we hypothesized that epigenetic regulation of ID4 gene might affect tumor differentiation and progression of CRC. The relationship between ID4 promoter hypermethylation and mRNA transcription, protein expression levels, and clinicopathological characteristics was determined.

Two of the three CRC cell lines had fully hypermethylated ID4 genes and consequently ID4 mRNA expression was inactivated. Bisulfite sequencing showed a concordance of methylation-specific PCR results and promoter hypermethylation. Only LOVO was partially methylated; it has both a methylated allele and an unmethylated allele and had been shown to have ID4 mRNA expression. These findings support the hypothesis that ID4 gene can be inactivated by promoter hypermethylation and CRC can have biallelic methylation. ID4 re-expression studies after 5Aza treatment showed that hypermethylation of the promoter region silenced expression of ID4 gene in CRC cell lines. The GAPDH mRNA was decreased after 5Aza treatment. However, this influence was compensated in the ratios of mRNA expression levels of ID4 and GAPDH, and the analysis was not affected.

To show that aberrant hypermethylation down-regulates ID4 protein expression level in CRCs, we did immunohistochemistry study on a subset of specimens that were methylated or unmethylated by methylation-specific PCR. ID4 protein was diffusely expressed in cytoplasm of nonmalignant epithelium, adenomas, and unmethylated CRCs, but it tended to be unexpressed in hypermethylated CRCs. Concordance between immunohistochemistry and methylation-specific PCR results showed that aberrant hypermethylation of ID4 down-regulated protein expression.

Methylation analysis on tissue specimens was done in a blinded fashion without any clinical information. The methylation status was determined by methylation-specific PCR based on the intensity ratio of the methylation-specific and unmethylation-specific peaks by automated capillary array electrophoresis system with analysis software. Because methylation-specific PCR can detect a very small percentage of methylated DNA in abundant unmethylated DNA, the methylation-specific PCR results were methylation-positive, even if only a small part of the microdissected tumor cells was hypermethylated. Aberrant hypermethylation was not found in normal colonic epithelia and adenomas, whereas 53% of primary CRCs and 73% of liver metastases were hypermethylated. The frequency of hypermethylation increased with CRC progression. This trend supports the concept of multi-step colorectal tumorigenesis (1, 40), in which genetic alterations accumulate during tumor progression. ID4 gene could be a putative tumor suppressor gene of CRC, which is epigenetically inactivated by promoter hypermethylation at a later stage of cancer development. The absence of hypermethylation in adenomas, which are considered to be precursors of CRC (1, 40), and the high frequency of hypermethylation in primary CRCs support the concept that ID4 downregulation is related to the malignant transformation of neoplastic tumor cells.

Multivariate analysis by Cox's proportional hazard model identified hypermethylation of ID4 as a significant independent risk factor of poor prognosis after curative surgical resection. Surprisingly, ID4 methylation status had higher impact on prognosis than lymph node metastasis, the most important prognostic risk factor for patients with curatively resected primary CRCs. Many tumor-related genes that are epigenetically inactivated in CRC tumor cells by promoter region hypermethylation, such as p16, APC, VHL, and hMLH1 (4-10), have been identified, but the prognostic utility of these methylated genes in primary tumors have not been well described. Our results indicate that ID4 hypermethylation can be used as a prognostic marker for CRC patients.

Univariate analysis and multivariate logistic regression analysis showed that methylation status significantly correlated with histopathological tumor grade. Histopathological tumor grade of CRC is an independent prognostic factor. At present, no regulatory gene for CRC cell differentiation via inhibition of specific transcription factors has been identified, but ID4 protein may have a regulatory function. The mechanisms by which the down-regulation of ID4 protein results in unfavorable prognosis are not clear, but it is likely that ID4 down-regulation promotes dedifferentiation and proliferation of CRC cells. ID4 protein may inhibit DNA binding of bHLH transcription factors that are involved in tumor cell dedifferentiation. Interestingly, some methylated tumors that contained both moderately differentiated and poorly differentiated areas stained positive for ID4 protein in the moderately differentiated area but negative in poorly differentiated area by immunohistochemistry. This heterogeneity in the ID4 protein level suggests that protein down-regulation may have induced tumor cell dedifferentiation. It is unknown whether ID4 silencing is directly linked to dedifferentiation or is just a confounding factor of the histologic grade at this time. Additional investigation is needed to reveal the mechanisms by which ID4 expression contributes to tumor cell differentiation in CRC progression.

In this study, it was shown that ID4 of CRC is epigenetically down-regulated. It has been also reported that ID4 is not expressed in certain human breast cancer tissues (41). However, previous animal studies have reported contrary findings showing that ID4 regulates mammary epithelial cell growth and differentiation and is overexpressed in rat mammary gland carcinomas (42). These observations suggest that the regulatory mechanisms of ID4 gene function may be differential in malignant tumors.

In conclusion, hypermethylation of the promoter region down-regulates ID4 at the mRNA level in CRC cell lines and at the protein level in clinical specimens. The frequency of hypermethylation is high in primary and metastatic CRCs compared with normal epithelium and adenoma. These results support ID4 as a potential tumor suppressor gene that may play an important role in CRC progression. ID4 transcription inactivation is associated with poorer differentiation of CRC and with unfavorable prognosis. ID4 hypermethylation can be used as a prognostic marker independent of TNM scores or stage of CRC.

REFERENCES

1. Kinzler K W, Vogelstein B. Lessons from hereditary colorectal cancer. Cell 1996; 87:159-70.
2. White R L. Tumor suppressing pathways. Cell 1998; 92:591-2.
3. Peltomaki P, de la Chapelle A. Mutations predisposing to hereditary nonpolyposis colorectal cancer. Adv Cancer Res 1997; 71:93-119.
4. Baylin S B, Herman J G, Graff J R, Vertino P M, Issa J P. Alterations in DNA methylation: a fundamental aspect of neoplasia. Adv Cancer Res 1998; 72:141-96.
5. Jones P A. The DNA methylation paradox. Trends Genet 1999; 15: 34-7.
6. Deng G, Chen A, Hong J, Chae H S, Kim Y S. Methylation of CpG in a small region of the hMLH1 promoter invariably correlates with the absence of gene expression. Cancer Res 1999; 59:2029-33.
7. Esteller M, Sparks A, Toyota M, et al. Analysis of adenomatous polyposis coli promoter hypermethylation in human cancer. Cancer Res 2000; 60:4366-71.
8. Robertson K D, Jones P A. DNA methylation: past, present and future directions. Carcinogenesis (Lond) 2000; 21:461-7.
9. Xiong Z, Wu A H, Bender C M, et al. Mismatch repair deficiency and CpG island hypermethylation in sporadic colon adenocarcinomas. Cancer Epidemiol Biomark Prev 2001; 10:799-803.
10. Herman J G. Hypermethylation pathways to colorectal cancer. Implications for prevention and detection. Gastroenterol Clin North Am 2002; 31:945-58.
11. Sanchez-Cespedes M, Esteller M, Hibi K, et al. Molecular detection of neoplastic cells in lymph nodes of metastatic colorectal cancer patients predicts recurrence. Clin Cancer Res 1999; 5:2450-4.
12. Sidransky D. Emerging molecular markers of cancer. Nat Rev Cancer 2002; 2:210-9.
13. Jones P A. DNA methylation errors and cancer. Cancer Res 1996; 56:2463-7.
14. Esteller M, Herman J G. Cancer as an epigenetic disease: DNA methylation and chromatin alterations in human tumours. J Pathol 2002; 196:1-7.
15. Herman J G, Baylin S B. Gene silencing in cancer in association with promoter hypermethylation. N Engl J Med 2003; 349:2042-54.
16. Pagliuca A, Bartoli P C, Saccone S, Della Valle G, Lania L. Molecular cloning of ID4, a novel dominant negative helix-loop-helix human gene on chromosome 6p21.3-p22. Genomics 1995; 27:200-3.
17. Massari M E, Murre C. Helix-loop-helix proteins: regulators of transcription in eucaryotic organisms. Mol Cell Biol 2000; 20:429-40.

18. Jen Y, Manova K, Benezra R. Expression patterns of Id1, Id2, and Id3 are highly related but distinct from that of Id4 during mouse embryogenesis. Dev Dyn 1996; 207:235-52.

19. Jen Y, Manova K, Benezra R. Each member of the Id gene family exhibits a unique expression pattern in mouse gastrulation and neurogenesis. Dev Dyn 1997; 208:92-106.

20. Kee Y, Bronner-Fraser M. Id4 expression and its relationship to other Id genes during avian embryonic development. Mech Dev 2001; 109:341-5.

21. Benezra R, Rafii S, Lyden D. The Id proteins and angiogenesis. Oncogene 2001; 20:8334-41.

22. Rivera R, Murre C. The regulation and function of the Id proteins in lymphocyte development. Oncogene 2001; 20:8308-16.

23. Zebedee Z, Hara E. Id proteins in cell cycle control and cellular senescence. Oncogene 2001; 20:8317-25.

24. Wilson J W, Deed R W, Inoue T, et al. Expression of Id helix-loophelix proteins in colorectal adenocarcinoma correlates with p53 expression and mitotic index. Cancer Res 2001; 61:8803-10.

25. Kleeff J, Ishiwata T, Friess H, et al. The helix-loop-helix protein Id2 is overexpressed in human pancreatic cancer. Cancer Res 1998; 58: 3769-72.

26. Wice B M, Gordon J I. Forced expression of Id-1 in the adult mouse small intestinal epithelium is associated with development of adenomas. J Biol Chem 1998; 273:25310-9.

27. Morrow M A, Mayer E W, Perez C A, Adlam M, Siu G. Overexpression of the Helix-Loop-Helix protein Id2 blocks T cell development at multiple stages. Mol Immunol 1999; 36:491-503.

28. Vandeputte D A, Troost D, Leenstra S, et al. Expression and distribution of id helix-loop-helix proteins in human astrocytic tumors. Glia 2002; 38:329-38.

29. Arnold J M, Mok S C, Purdie D, Chenevix-Trench G. Decreased expression of the Id3 gene at 1p36.1 in ovarian adenocarcinomas. Br J Cancer 2001; 84:352-9.

30. Deleu S, Savonet V, Behrends J, Dumont J E, Maenhaut C. Study of gene expression in thyrotropin-stimulated thyroid cells by cDNA expression array: ID3 transcription modulating factor as an early response protein and tumor marker in thyroid carcinomas. Exp Cell Res 2002; 279:62-70.

31. Kondo T, Raff M. The Id4 HLH protein and the timing of oligodendrocyte differentiation. EMBO J. 2000; 19:1998-2007.

32. Chan A S, Tsui W Y, Chen X, et al. Downregulation of ID4 by promoter hypermethylation in gastric adenocarcinoma. Oncogene 2003; 22:6946-53.

33. Spugnardi M, Tommasi S, Dammann R, Pfeifer G P, Hoon D S. Epigenetic inactivation of RAS association domain family protein 1 (RASSF1A) in malignant cutaneous melanoma. Cancer Res 2003; 63: 1639-43.

34. Jones P A. Altering gene expression with 5-azacytidine. Cell 1985; 40:485-6.

35. Hoon D S, Spugnardi M, Kuo C, et al. Profiling epigenetic inactivation of tumor suppressor genes in tumors and plasma from cutaneous melanoma patients. Oncogene 2004; 23:4014-22.

36. Greene L F, Page L D, Fleming D I, Fritz A, Balch M C. AJCC Cancer Staging Manual. 6th ed., New York: Springer-Verlag; 2002. p. 113-24.

37. Shinozaki M, Fujimoto A, Morton D L, Hoon D S. Incidence of BRAF oncogene mutation and clinical relevance for primary cutaneous melanomas. Clin Cancer Res 2004; 10:1753-7.

38. Pagliuca A, Cannada-Bartoli P, Lania L. A role for Sp and helix-loop-helix transcription factors in the regulation of the human Id4 gene promoter activity. J Biol Chem 1998; 273:7668-74.

39. Takeuchi H, Kuo C, Morton D L, Wang H J, Hoon D S. Expression of differentiation melanoma-associated antigen genes is associated with favorable disease outcome in advanced-stage melanomas. Cancer Res 2003; 63:441-8.

40. Vogelstein B, Fearon E R, Hamilton S R, et al. Genetic alterations during colorectal-tumor development. N Engl J Med 1988; 319:525-32.

41. Welcsh P L, Lee M K, Gonzalez-Hernandez R M, et al. BRCA1 transcriptionally regulates genes involved in breast tumorigenesis. Proc Natl Acad Sci USA 2002; 99:7560-5.

42. Shan L, Yu M, Qiu C, Snyderwine E G. Id4 regulates mammary epithelial cell growth and differentiation and is overexpressed in rat mammary gland carcinomas. Am J Pathol 2003; 163:2495-502.

EXAMPLE II

Aberrant Hypermethylation of ID4 Gene Promoter Region Increases Risk of Lymph Node Metastasis in T1 Breast Cancer We hypothesized that additional information about genetic alteration of cancer cells could be helpful for a prediction of nodal metastasis, and aimed to find new genetic markers of nodal metastasis. As advanced primary cancers have more lymphovascular invasion than early stage cancers, which directly causes metastasis and may mask the impacts of the genetic alterations, we considered that early cancers are more suitable for a study of assaying a new genetic marker that influence on regional lymph node metastasis. In addition, because genetic abnormalities are accumulated during cancer progression, we considered that early cancers would have simple correlations between genetic alterations and biological behavior.

We hypothesized that ID4 may have a putative tumor suppressive role in early stages of breast cancer progression, and epigenetic inactivation of ID4 gene by promoter hypermethylation might favor regional lymph node metastasis. To examine this hypothesis, we assessed the relation between methylation status of ID4 promoter region and mRNA transcription level in breast cell lines and the correlation between ID4 hypermethylation and regional lymph node metastasis of T1 primary breast cancers.

Materials and Methods

Cell lines. Six established breast cancer cell lines (MCF-7, T-47D, BT-20, BT-549, 734B and MDA-MB-231), and an immortalized breast epithelial cell line HBL-100 from American Type Culture Collection (ATCC) (Manassas, Va.), and one breast cancer cell line (BR2) established in JWCI were analyzed in this study. Additionally, three established colorectal cancer cell lines SW480, DLD1 and LOVO from ATCC were also analyzed. Genomic DNA was extracted from cells as previously described (Spugnardi et al., 2003). Total RNA was extracted using TRI Reagent (Molecular Research Center, Inc., Cincinnati, Ohio) according to the manufacturer's protocol. Quality and quantity of extracted DNA and total RNA were measured by UV absorption spectrophotometry.

Tissue specimens and clinicopathology. All specimens were from formalin-fixed paraffin-embedded archived tissues (PEAT) of female patients who underwent segmental or total mastectomy with sentinel lymph node biopsy and/or axillary lymph node dissection for T1 invasive breast cancer between 1996 and 2001 at Saint John's Health Center, Santa Monica. Lymph node metastasis was diagnosed with conventional H&E staining. Case-control methodology was adopted to reduce variations associated with tumor size and patient age. The N (+) group consisted of 24 patients with axillary lymph node metastasis; the N (−) group consisted of 36 patients without lymph node metastasis, who were selected by matched-sampling to achieve the equivalent distribution of tumor size and age with the N (+) group. The H&E-confirmed normal mammary gland tissues were obtained from the same sections of 11 cancer specimens. Tumors were classified and staged according to the guidelines set by the American Joint Committee on Cancer (AJCC). All patients in this study were consented according to the guidelines set forth by Saint John's Health Center and JWCI human subjects Institutional Review Board (IRB) committee.

Two 5-μm and one 10-μm sections were cut with a microtome from the PEAT blocks under sterile conditions as previously described (Umetani et al., 2004b). One 5-μm section for each tumor was stained with H&E after deparaffinization as references of microdissection. For DNA methylation analysis, the tumor or normal tissues were precisely microdissected under a microscope from one 5-μm section as previously described (Umetani et al., 2004b) and subsequently digested with 50 ul of proteinase K containing lysis buffer. To compare the mRNA transcription level between hypermethylated cancers and unmethylated cancers, 10 specimens of each groups were selected and the tumor tissues were precisely microdissected under a microscope from one 10-μm section for each specimen as previously described (Umetani et al., 2004a) and subsequently mRNA was extracted with RNAwiz RNA Isolation Kit (Ambion, Austin, Tex.) following the manufacturer's protocol.

Detection of hypermethylation. The methylation status of ID4 gene promoter region was evaluated by MSP, the specificity of which had been previously established by sodium bisulfite modification (SBM) sequencing (Umetani et al., 2004b).

Figure 5:
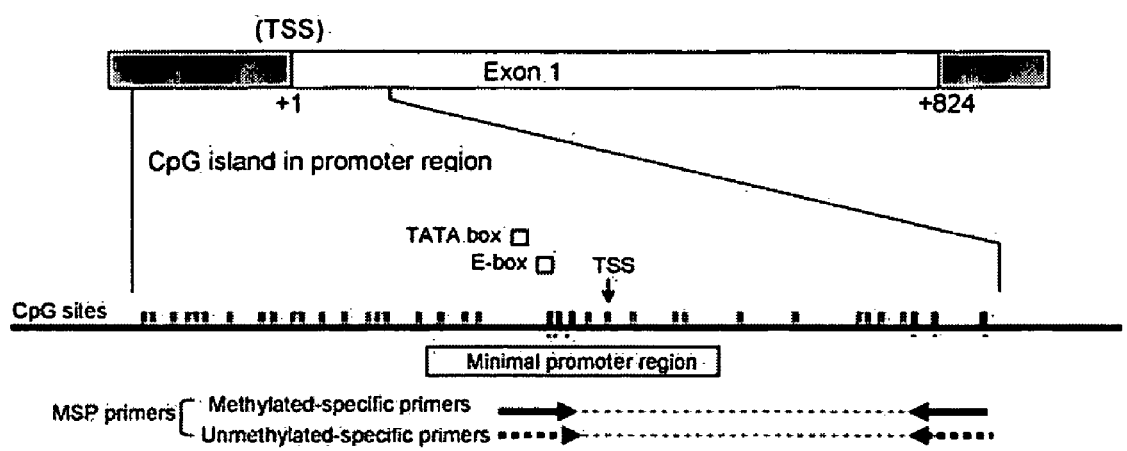
FIG. 5. Diagram of the promoter region of ID4 gene and the primer design for MSP. CpG sites in the annealing site of MSP primers are indicated with '*'. Forward primers cover the TATA box, E-box and three CpG sites in the ID4 minimal promoter region. TSS: transcription start site.

SBM was applied on extracted genomic DNA of tissue specimens and cell lines for MSP (Spugnardi et al., 2003). Methylation status of ID4 promoter region was analyzed by MSP as previously described (Umetani et al., 2004b). The MSP primer sets were highly specific for detection of the methylation status of ID4 promoter (FIG. 5). Forward primers for MSP covered the TATA box, E-box and three CpG sites in the ID4 minimal promoter region (−48 to +32) (Umetani et al., 2004b). The methylation-specific primer set was as follows: forward, 5'-D4-TTTTATAAATATAGTTGCGCGGC-3'; reverse, 5'-GAAACTCCGACTAAACCCGAT-3'. The unmethylation-specific primer set was as follows: forward, 5'-D3-TTTTATAAATATAGTTGTGTGGTGG-3'; reverse, 5'-TCAAAACTCCAACTAAACCCAAT-3'. Accuracy and reproducibility of these MSP primer sets had been confirmed by sodium bisulfite sequencing on peripheral blood leukocytes and hypermethylated cancer cell lines using primer sets as previously described (Chan et al., 2003). PCR amplification was performed in a 10-ul reaction volume with 1 ul template for 40 cycles of 30 s at 94° C., 30 s at 58° C. and 30 s at 72° C., followed by a 7-min final extension at 72° C. $Mg^{2+}$ concentration was 1.5 mM for methylated-specific and 2.5 mM for unmethylated-specific primer sets. Primer concentration was 0.1 uM for methylated-specific and 0.4 uM for unmethylated-specific primer sets. PCR products were detected and analyzed by CEQ 8000XL CAE system (Beckman Coulter, Inc., Fullerton, Calif.) using CEQ 8000 software version 6.0 (Beckman Coulter) as previously described (Hoon et al., 2004). Methylation status of each specimen was determined by MI, which was calculated from the fluorescent signal intensities of methylated (M) and unmethylated (U) PCR products by following formula: MI=M/(M+U). The range of MI was from 0.0 in completely unmethylated template DNA to 1.0 in completely methylated template DNA. MI was measured twice for each specimen; values larger than 0.1 corresponded to hypermethylation.

Analysis of mRNA transcription level. Reverse-transcriptase reactions were performed on 1.0 μg of extracted total RNA using Moloney murine leukemia virus reverse-transcriptase (Promega, Madison, Wis.) with oligo-dT primers, as previously described (Takeuchi et al., 2003). For clinical specimens, random primers were additionally used. QRT assay was performed on the iCycler iQ Real-Time thermocycler detection system (Bio-Rad Laboratories, Hercules, Calif.), as previously described (Takeuchi et al., 2003). For each PCR, the reaction mixture consisted of cDNA template synthesized by reverse-transcription from 250 ng of total RNA, 0.5 μM of forward primer (5'-CGCTCACTGCGCT-CAACAC-3'), 0.5 μM of reverse primer (5'-TCAGGCGGC-CGCACACCT-3'), and 0.6 μM of fluorescence resonance energy transfer (FRET) probe (5'-FAM-CATTCTGTGC-CGCTGAGCCG-BHQ-3'). PCR amplification was performed in a 20-ul reaction volume 3 mM of $Mg^{2+}$ for 45 cycles: 30 s at 94° C., 30 s at 58° C., and 30 s at 72° C. Absolute copy numbers were determined by a standard curve with serial dilutions ($10^8$ to $10^0$ copies) of DNA containing ID4 cDNA sequence. Analysis without templates was performed as a negative control in each study. PCR products were electrophoresed on 2% agarose gels to confirm product size and absence of non-specific bands. The transcription level of the house-keeping gene GAPDH was measured by qRT as an internal reference with a standard curve to determine the integrity of template RNA for all specimens. The relative mRNA level of ID4 was calculated as: absolute copy number of ID4/absolute copy number of GAPDH in 250 ng of total RNA (Takeuchi et al., 2003). Median values of triplicated quantification were used for analysis.

Statistical Analysis. The matched background parameters (age, tumor size) were compared between N (+) group and N (−) group by the Student's t test. Frequency of ID4 hypermethylation in normal mammary gland tissues was compared with those in N (+) cancers and N (−) cancers by Fisher's exact test. Contribution of ID4 methylation status and other clinicopathological characteristics to lymph node metastasis was analyzed by univariate and multivariate nominal logistic regression. For comparison of mRNA level in cancer specimens, Wilcoxon's rank-sum test was used. The statistical package SAS JMP ver 5.1 (SAS Institute Inc., Cary, N.C.) was used to conduct statistical analyses. A two-tailed P value <0.05 was considered significant.

Results

Figure 6:
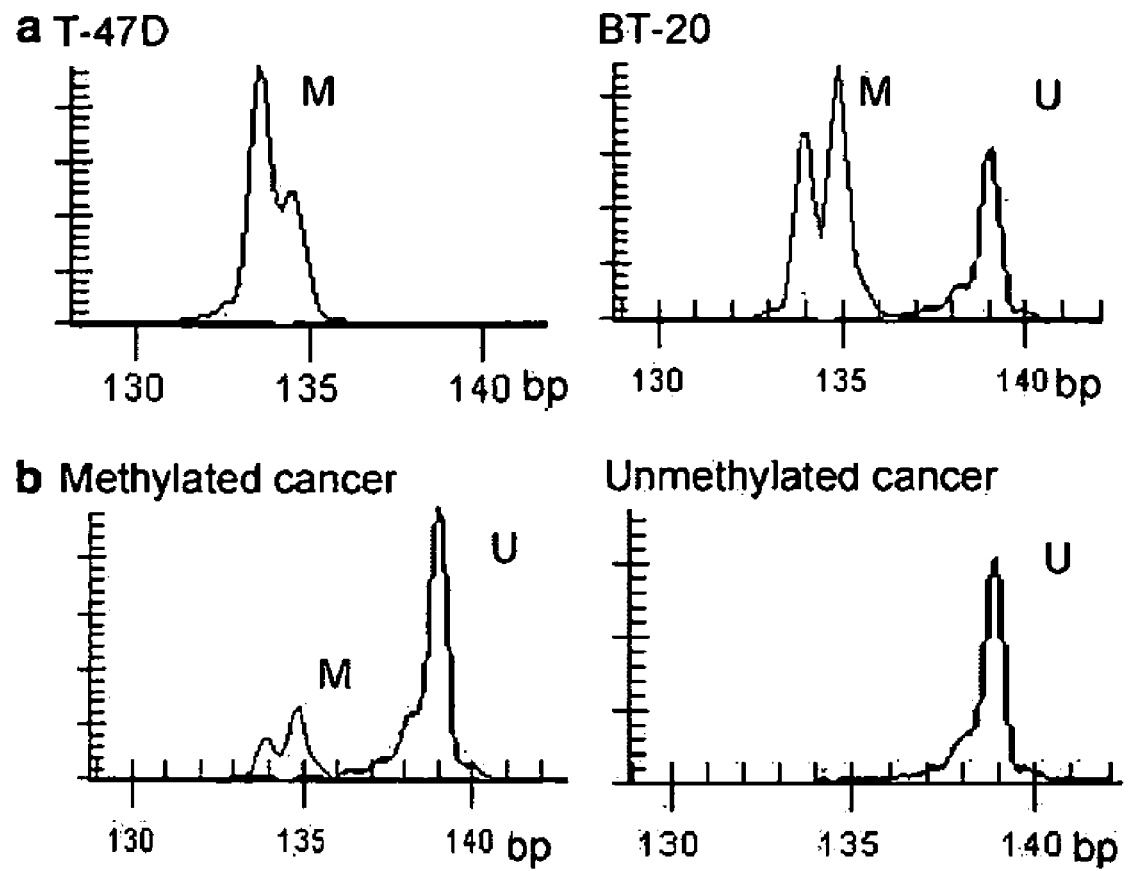
FIG. 6. Representative capillary array electrophoresis (CAE) results of methylation-specific PCR (MSP). Representative MSP results of breast cancer cell lines T-47D and BT-20 (a) and T1 breast cancer specimens (b). The fluorescent intensity shown on the vertical axis represents the amount of PCR amplicon assessed by CAE. The horizontal axis represents the fragment size of the amplicon. 'M' peak: methylated-specific product of MSP; 'U' peak: unmethylated-specific product of MSP.
Figure 7:
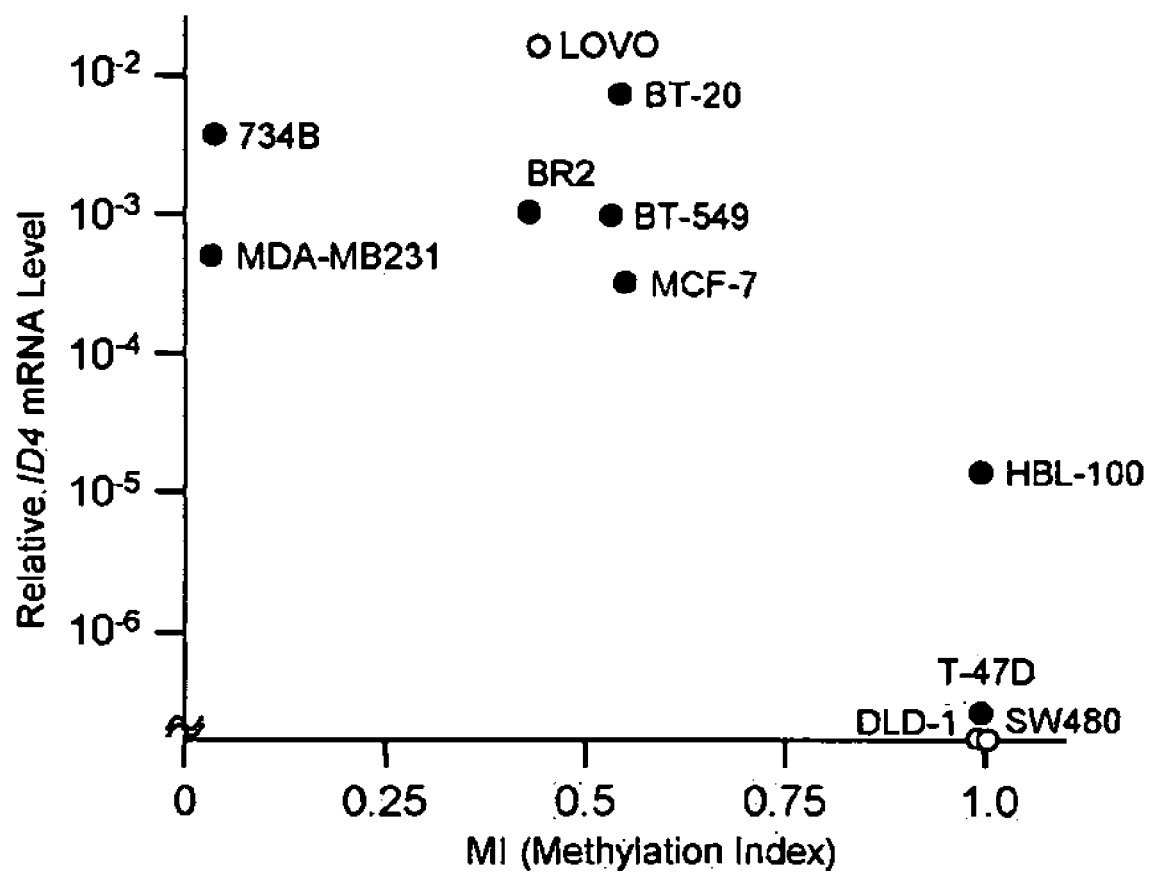
FIG. 7. ID4 transcription level and MI in cell lines. ID4 mRNA transcription level and MI in eight breast cell lines (•) and additional three colorectal cancer cell lines (o). Vertical axis represents the relative ID4 mRNA level normalized by GAPDH mRNA level in log scale. Horizontal axis represents MI values. Cell lines T-47D, HBL-100, SW480, and DLD1 showed only methylated-specific peaks (MI=1.0) and mRNA transcription was highly suppressed. Partially hypermethylated cell lines (MI=0.43~0.55) and two unmethylated cell lines (MI=0.02, 0.03) had relatively high level of mRNA.

Cell line analysis. We initially assessed established breast cell lines to determine and optimize the methylation-specific PCR (MSP) assay for ID4 promoter region (FIG. 5). Representative MSP results of ID4 promoter region in breast cancer cell lines (T-47D and BT-20) are shown in FIG. 6a in combination with those in breast cancer specimens in FIG. 6b. Among the eight breast cell lines studied, two cell lines (T-47D and HBL-100) were fully methylated showing only methylated-specific peaks (methylation index (MI)=1.0), and four cell lines (MCF-7, BT20, BT549, and BR2) were partially methylated showing both methylated-specific and unmethylated-specific peaks (MI=0.55, 0.55, 0.53, and 0.43, respectively), and two cell lines (734B and MDA-MB231)

were unmethylated (MI=0.03 and 0.02, respectively) by MSP. Additional three colorectal cancer cell lines showed that two cell lines (SW480, DLD1) were fully methylated (MI=1.0) and one cell line (LOVO) was partially methylated (MI=0.45). Relative copy numbers of ID4 mRNA were quantified by quantitative real-time RT-PCR (qRT) on these cell lines, and it was shown that ID4 transcription level was highly suppressed in the fully methylated cell lines (FIG. 7). This observation indicated that ID4 mRNA transcription was inactivated by homozygous hypermethylation of promoter region.

Figure 8:
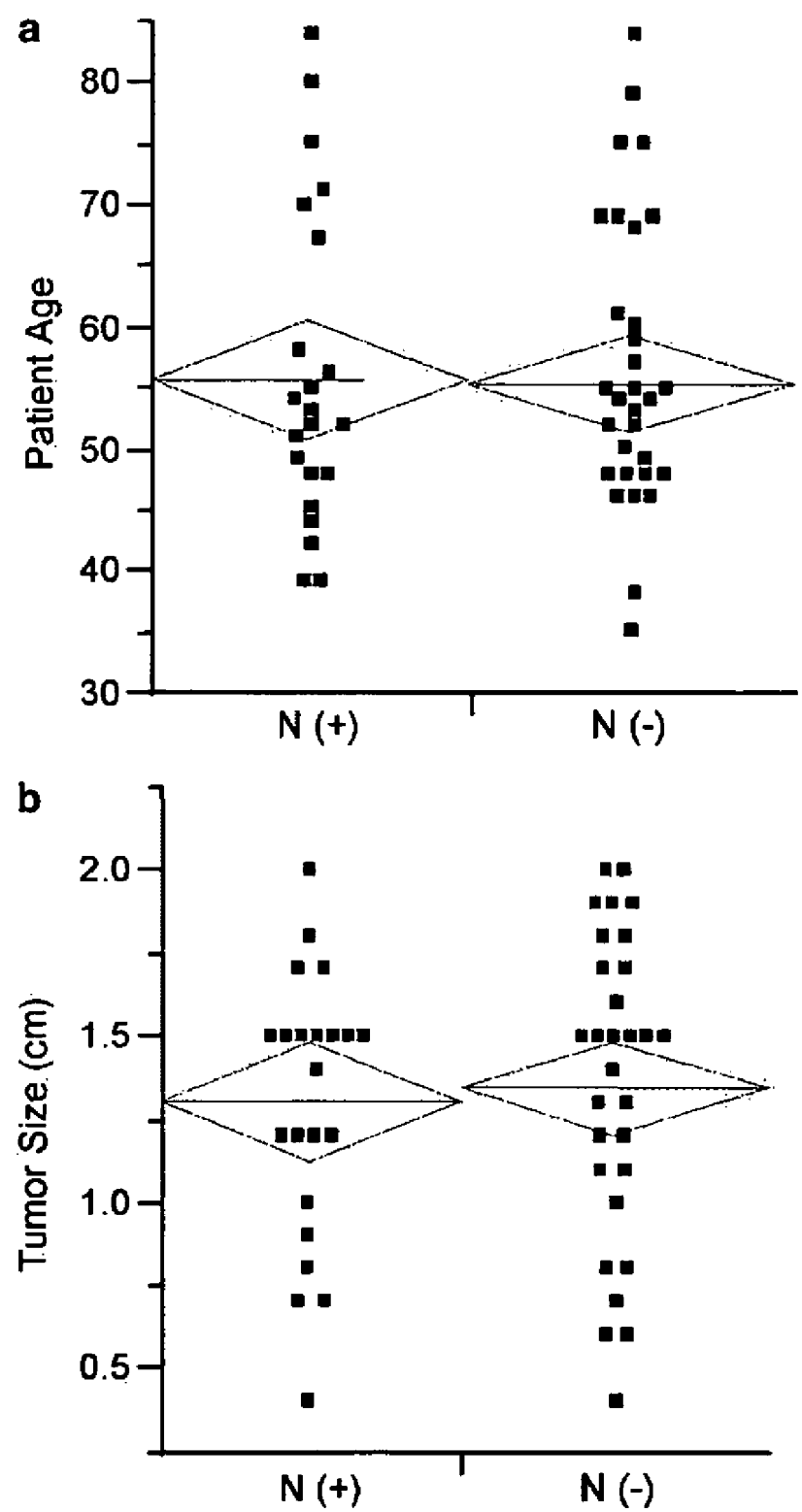
FIG. 8. Matched background parameters in T1 breast cancers. Distribution of size and patient age, matched background parameters between N (+) group and N (−) group, with mean diamonds indicating group mean values and 95% confidence intervals of mean. Each dot represents the age and tumor size of each tumor.

Analysis of clinical specimens. To determine the clinical contribution of ID4 hypermethylation to tumor aggressiveness, we compared the methylation status of ID4 gene promoter region in primary tumors from patients with and without nodal metastasis. Case (node-positive, N (+)) and control (node-negative, N (−)) groups were matched by patient age and tumor size. Age at tumor resection (mean±s.e.m., years) was 56.0±2.4 in the N (+) group and 55.4±2.0 in the N (−) group (P=0.85, Student's t test) (FIG. 8a). Size of the primary breast cancer (mean±s.e.m.) was 1.30±0.09 cm in the N (+) group and 1.36±0.07 cm in the N (−) group (P=0.56, Student's t test) (FIG. 8b).

Figure 9:
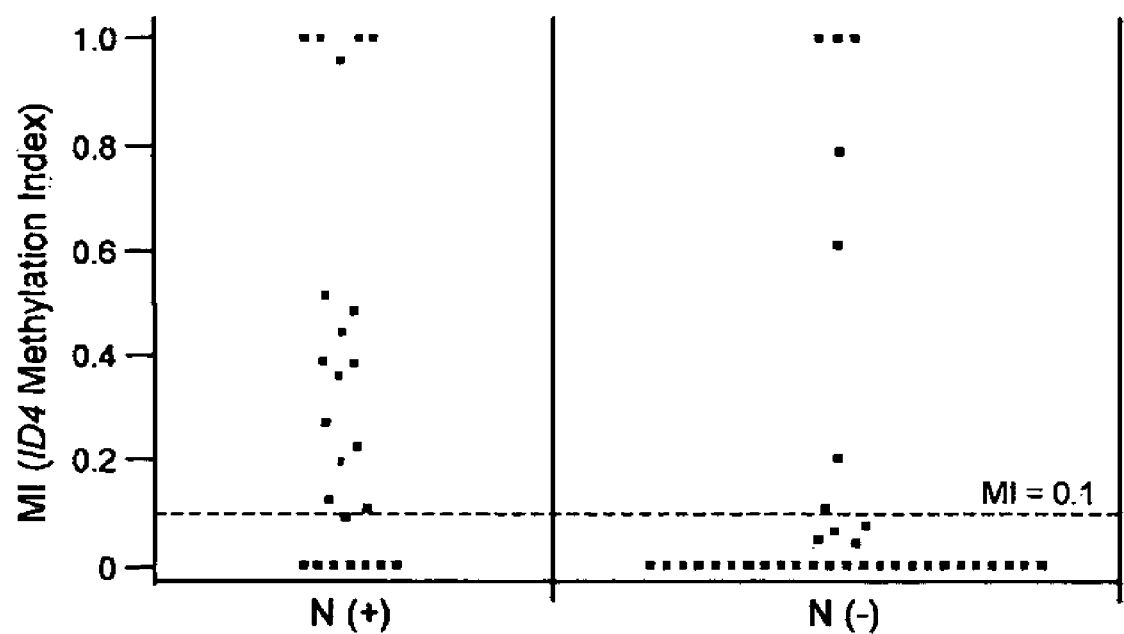
FIG. 9. MI (methylation index) distribution in N (+) and N (−) breast cancers. Methylation status of each specimen was determined by MI calculated from the fluorescent signal intensities of MSP. MI was measured twice for each specimen; values larger than 0.1 corresponded to hypermethylation. Dotted horizontal line represents the threshold level of hypermethylation. Each dot represents the MI of each tumor.

Representative MSP results of ID4 promoter region in breast cancer specimens are shown in FIG. 6b. Hypermethylation of the ID4 promoter region was identified in 16 of 24 (67%) N (+) cancers, 7 of 36 (19%) N (−) cancers, and 2 of 11 (18%) normal mammary gland specimens obtained from the tumor-adjacent tissue (FIG. 9). The frequency of ID4 hypermethylation was similar in N (−) cancers and histopathologically normal mammary glands, but significantly higher in N (+) cancers than in normal mammary glands (P=0.012, Fisher's exact test).

Univariate logistic regression analysis for lymph node metastasis with ID4 methylation status and clinicopathological risk factors identified ID4 methylation status as a significant (OR 8.29, CI: 2.65-28.9; P=0.0005) risk factor (Table 6). Lymphovascular invasion and HER2/neu values tended to correlate with nodal metastasis (P=0.067 and 0.097, respectively). No relation was found between the primary tumor's ID4 methylation status and its histologic grade (well/moderate/poor) or type (invasive ductal/invasive lobular), ER status, DNA ploidy, S-phase, or Ki-67 values. For multivariate logistic regression analysis, we selected covariates by forward stepwise selection with an entering cut-off P value of 0.25 from ID4 methylation status and the above-described risk factors. Accordingly, ID4 methylation status, lymphovascular invasion, and HER2/Neu value were selected and incorporated into the regression model, and ID4 methylation status had significance (OR 13.1, CI: 3.50-61.8; P=0.0004) and HER2/neu had borderline significance (P=0.053) for lymph node metastasis (Table 7).

TABLE 6

Univariate Nominal Logistic Regression for Lymph Node Metastasis

| Variable | n* | Odds ratio (95% CI) | P-value |
| --- | --- | --- | --- |
| Histologic grade (poor/well/moderate) | 60 | 1.43 (0.49–4.19) | 0.51 |
| Histologic type (invasive ductal/invasive lobular) | 60 | 0.88 (0.18–4.8) | 0.87 |
| Lymphovascular invasion (yes/no) | 57 | 3.62 (0.94–15.7) | 0.067 |
| ER (positive/negative) | 60 | 0.68 (0.19–2.26) | 0.54 |
| DNA ploidy (diploid/aneuploid) | 60 | 0.76 (0.27–2.13) | 0.60 |
| S phase (%) | 57 | 0.96 (0.11–7.51) | 0.97 |
| Ki-67 | 47 | 0.31 (0.01–4.30) | 0.41 |
| HER2/neu | 60 | 3.67 (0.81–18.3) | 0.097 |
| ID4 methylation (methylated/unmethylated) | 60 | 8.29 (2.65–28.9) | 0.0005 |

*Number or available cases

TABLE 7

Multivariate Nominal Logistic Regression for Lymph Node Metastasis (n = 57)
Table 2 Multivariate nominal logistic regression for lymph node metastasis (n = 57)

| Variable* | Odds ratio (95% CI) | P-value |
| --- | --- | --- |
| Lymphovascular invasion (yes/no) | 3.30 (0.66–19.0) | 0.156 |
| HER2/neu | 6.73 (1.04–53.5) | 0.053 |
| ID4 methylation (methylated/unmethylated) | 13.1 (3.50–61.8) | 0.0004 |

*Selected by forward stepwise selection with an entering cutoff P-value of 0.25

Figure 10:
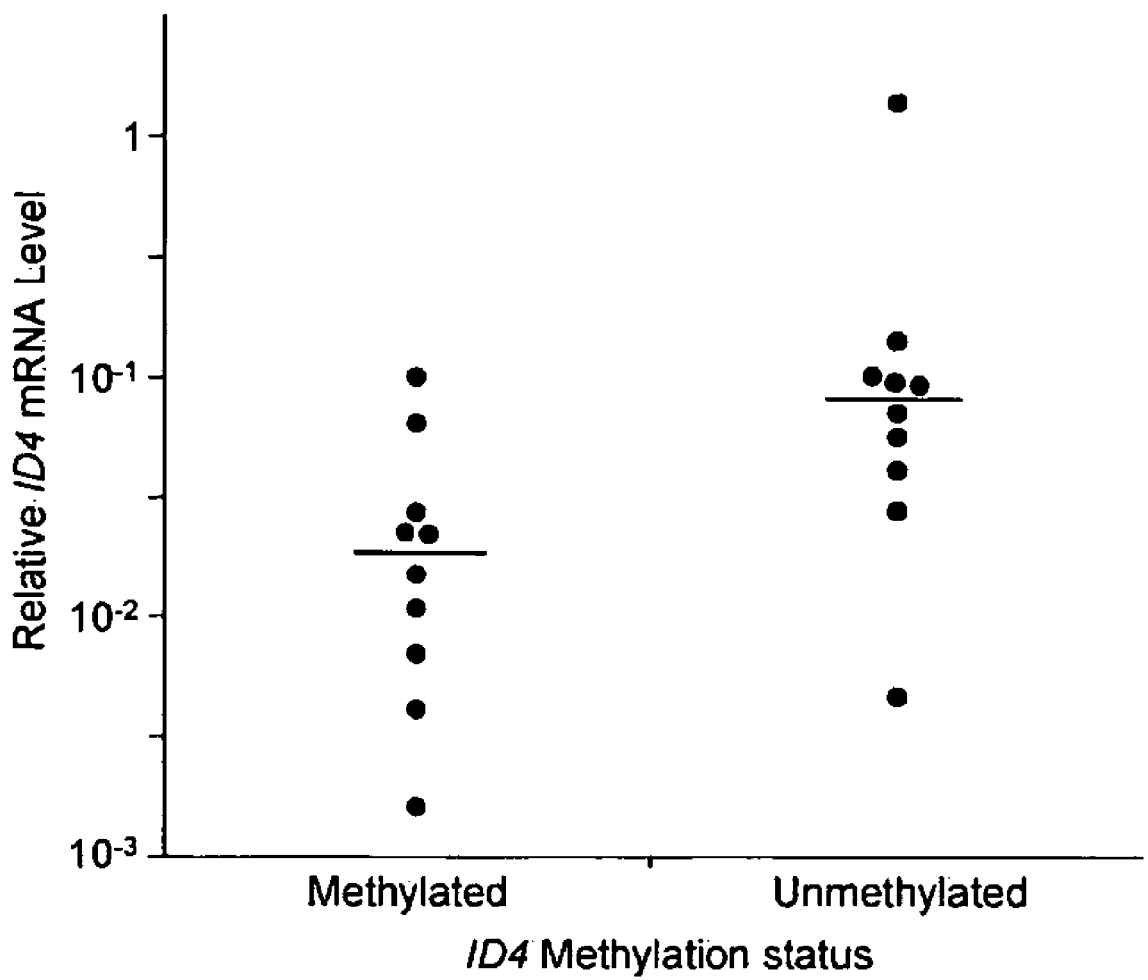
FIG. 10. ID4 mRNA level in hypermethylated and unmethylated breast cancers. Transcription levels of mRNA in 10 hypermethylated and 10 unmethylated breast cancer specimens. Vertical axis represents the relative ID4 mRNA level normalized by GAPDH mRNA level in log scale. Hypermethylated specimens had significantly lower transcription level than unmethylated specimens ($P=0.014$, Wilcoxon's rank sum test).

To determine whether the ID4 mRNA level in clinical cancer specimens was suppressed by promoter hypermethylation, we assessed 10 specimens from hypermethylated cancers (MI range: 0.27-1.0, median: 0.44) and 10 specimens from unmethylated cancers (MI=0.0). Relative ID4 mRNA level was significantly lower in hypermethylated cancers (range: 0.0016-0.099, median: 0.018) than that in unmethylated cancers (range: 0.0045-1.31, median: 0.080) (P=0.014, Wilcoxon's rank sum test) (FIG. 10).

Discussion

It is very important to find risk factors of nodal metastasis especially in early stage primary breast cancers, because precise prediction of potential metastatic ability of the tumor could help the appropriate decision making of treatment. We considered that molecular markers for nodal metastasis might be more valuable than the conventional pathological risk factors (Brenin et al., 2001) because the genetic changes can identify malignant behavior in cancer cells. Such genetic or epigenetic alterations occurred in the early stage of the tumor development are potentially good prognostic markers. Therefore, we focused on T1 breast cancers. As lymph node metastasis is not frequent in T1 breast cancers, we used a case-control methodology to find the contribution of epigenetic modification of ID4 gene. Tumor size and age were matched because tumor size is one of the most important predictors of tumor behavior in breast cancer (Fisher et al., 1984; Fitzgibbons et al., 2000), and background aberrant hypermethylation increases with age (Toyota & Issa, 1999). We defined nodal metastasis based on staining with H&E as the gold standard in this study. We did not use special stains such as cytokeratin IHC because of the possibility of the detection of transported benign epithelial cells those lacking metastatic potential (Carter et al., 2000; Moore et al., 2004).

Because ID4 is a dominant inhibitor of transcription factors and might be a key controlling factor for cell differentiation, we hypothesized that epigenetic regulation of ID4 gene might affect progression of breast cancer. The relation between ID4 promoter hypermethylation and mRNA transcription was initially determined in breast cell lines. ID4 mRNA transcription was inactivated in the fully methylated two breast cell lines. Same inactivation was also observed in colorectal cancer cell lines. Fully hypermethylated cell lines supposedly have homozygous methylation or monozygous methylation plus allelic loss at the ID4 locus. These findings support the hypothesis that ID4 gene can be inactivated by promoter hypermethylation. Previously, the restoration by the demethylating agent 5-aza-cytidine treatment had been demonstrated in gastric (Chan et al., 2003) and colorectal (Umetani et al., 2004b) cell lines as a confirmation of the inactivating mechanism. The two breast cell lines (T47D and HBL-100) that are fully hypermethylated are known to be less invasive, and these results seemed to be inconsistent with the hypothesis that the epigenetic inactivation of ID4 contributes the aggressiveness of the cancer cells. However, because the characteristics of cell lines are determined by many kinds of genetic or epigenetic alteration, it is difficult to relate directly the cell characteristics to single gene expression. Further investigation for ID4 gene function in the breast cancer cells is mandatory as a future study.

Methylation status of cancer specimens was analyzed without knowledge of clinicopathological status, including nodal metastasis. Methylation was objectively determined according to the intensity ratio of methylated-specific and unmethylated-specific peaks quantified by automated capillary array electrophoresis (CAE) system. Because MSP can detect a very small percentage of methylated DNA in abundant unmethylated DNA (Herman et al., 1996), the MSP results would be positive even if only a small part of the microdissected tumor cells was hypermethylated. Frequency of aberrant hypermethylation of N (−) cancer specimens was lower than that of N (+) cancer specimens, which suggested that ID4 gene inactivation might enhanced the aggressiveness and risk of nodal metastasis. Furthermore, we demonstrated that hypermethylated breast primary cancer specimens have significantly lower mRNA level of ID4, indicating that ID4 transcription was similarly inactivated by promoter hypermethylation in clinical breast cancer specimens as the cell lines. However, the difference of mRNA level between the two groups was not prominent, suggesting that the entire cells in the hypermethylated tumors are not uniformly inactivated. Based on the hypothesis that primary breast cancers are genetically or epigenetically heterogeneous and metastasis occurs due to aggressive malignant clones, finding such aggressive clones amongst the other dominant clones within a tumor lesion with a sensitive genetic marker is clinically useful. If the ID4 suppression is an important mechanism for metastasis, detecting clones with ID4 suppression by quantifying the mRNA level is less sensitive. Therefore, we consider that detecting hypermethylated clones by highly sensitive methods such as MSP has greater potential for clinical utility than quantifying mRNA level.

Normal breast specimens showed approximately equivalent base line aberrant hypermethylation level as N (−) cancer specimens. Because the normal tissue was obtained from adjacent normal mammary glands of cancer specimens, there was a possibility that occult cancer cells might be contaminated. There was another possibility that ID4 hypermethylation in pre-malignant mammary gland might be related to the carcinogenesis.

ID4 has been shown to be a regulator of BRCA1 expression (Beger et al., 2001), and a negative co-regulation of ID4 and BRCA1 was reported in breast cancer cell lines (Welcsh et al., 2002). However, in primary breast cancers, ID4 expression was observed to be positively correlated with BRCA1 expression (Welcsh et al., 2002). Epigenetic inactivation of ID4 gene may disrupt the ID4-BRCA1 regulatory loop. ID4 was reportedly overexpressed in rat mammary gland carcinomas and positively correlates with proliferation, invasiveness, and tumor weight (Shan et al., 2003). Our results were contradictory to this animal study. Since ID4 can indirectly suppress many kinds of gene expression via downregulating bHLH transcription factors, the mechanism of ID4 function will be complicated. Further functional studies will elucidate the mechanisms of contribution of this gene to breast cancer development and/or progression.

In conclusion, this is the first report of ID4 promoter hypermethylation in breast cancer and its effect on lymph node metastasis. Hypermethylation of the promoter region appears to be a frequent phenomenon in human breast cancer and downregulates transcription of ID4 gene in breast cell lines and breast cancer tissues, and may increase the risk of lymph node metastasis. It is suggested that ID4 is a potential tumor suppressive gene that may play an important role in aggressiveness of tumor behavior. ID4 hypermethylation might prove useful as a genetic marker to predict early metastasis. Further investigation is needed to reveal the mechanisms by which ID4 inactivation contributes to tumor aggressiveness and promotes metastasis.

REFERENCES

Barth, A., Craig, P. H. & Silverstein, M. J. (1997). *Cancer,* 79, 1918-22.

Beger, C., Pierce, L. N., Kruger, M., Marcusson, E. G., Robbins, J. M., Welcsh, P., Welch, P. J., Welte, K., King, M. C., Barber, J. R. & Wong-Staal, F. (2001). *Proc Natl Acad Sci USA,* 98, 130-5.

Benezra, R., Rafii, S. & Lyden, D. (2001). *Oncogene,* 20, 8334-41.

Brenin, D. R., Manasseh, D. M., El-Tamer, M., Troxel, A., Schnabel, F., Ditkoff, B. A. & Kinne, D. (2001). *Ann Surg Oncol,* 8, 432-7.

Carter, B. A., Jensen, R. A., Simpson, J. F. & Page, D. L. (2000). *Am J Clin Pathol,* 113, 259-65.

Carter, C. L., Allen, C. & Henson, D. E. (1989). *Cancer,* 63, 181-7.

Chan, A. S., Tsui, W. Y., Chen, X., Chu, K. M., Chan, T. L., Li, R., So, S., Yuen, S. T. & Leung, S. Y. (2003). *Oncogene,* 22, 6946-53.

Esteller, M. & Herman, J. G. (2002). *J Pathol,* 196, 1-7.

Fisher, E. R., Anderson, S., Redmond, C. & Fisher, B. (1993). *Cancer,* 71, 2507-14.

Fisher, E. R., Fisher, B., Sass, R. & Wickerham, L. (1984). *Cancer,* 54, 3002-11.

Fitzgibbons, P. L., Page, D. L., Weaver, D., Thor, A. D., Allred, D. C., Clark, G. M., Ruby, S. G., O'Malley, F., Simpson, J. F., Connolly, J. L., Hayes, D. F., Edge, S. B., Lichter, A. & Schnitt, S. J. (2000). *Arch Pathol Lab Med,* 124, 966-78.

Herman, J. G. & Baylin, S. B. (2003). *N Engl J Med*, 349, 2042-54.

Herman, J. G., Graff, J. R., Myohanen, S., Nelkin, B. D. & Baylin, S. B. (1996). *Proc Natl Acad Sci USA*, 93, 9821-6.

Holland, P. A., Walls, J., Boggis, C. R., Knox, F., Baildam, A. D. & Bundred, N. J. (1996). *Br J Cancer*, 74, 1643-6.

Hoon, D. S., Spugnardi, M., Kuo, C., Huang, S. K., Morton, D. L. & Taback, B. (2004). *Oncogene*, 23, 4014-22.

Itahana, Y., Singh, J., Sumida, T., Coppe, J. P., Parrinello, S., Bennington, J. L. & Desprez, P. Y. (2003). *Cancer Res*, 63, 7098-105.

Jen, Y., Manova, K. & Benezra, R. (1996). *Dev Dyn*, 207, 235-52.

Jen, Y., Manova, K. & Benezra, R. (1997). *Dev Dyn*, 208, 92-106.

Jones, P. A. (1996). *Cancer Res*, 56, 2463-7.

Jones, P. A. (1999). *Trends Genet*, 15, 34-7.

Kee, Y. & Bronner-Fraser, M. (2001). *Mech Dev*, 109, 341-5.

Lin, C. Q., Singh, J., Murata, K., Itahana, Y., Parrinello, S., Liang, S. H., Gillett, C. E., Campisi, J. & Desprez, P. Y. (2000). *Cancer Res*, 60, 1332-40.

Massari, M. E. & Murre, C. (2000). *Mol Cell Biol*, 20, 429-40.

Moore, K. H., Thaler, H. T., Tan, L. K., Borgen, P. I. & Cody, H. S., 3rd. (2004). *Cancer*, 100, 929-34.

Pagliuca, A., Bartoli, P. C., Saccone, S., Della Valle, G. & Lania, L. (1995). *Genomics*, 27, 200-3.

Rivera, R. & Murre, C. (2001). *Oncogene*, 20, 8308-16.

Schoppmann, S. F., Schindl, M., Bayer, G., Aumayr, K., Dienes, J., Horvat, R., Rudas, M., Gnant, M., Jakesz, R. & Birner, P. (2003). *Int J Cancer*, 104, 677-82.

Shan, L., Yu, M., Qiu, C. & Snyderwine, E. G. (2003). *Am J Pathol*, 163, 2495-502.

Singh, J., Murata, K., Itahana, Y. & Desprez, P. Y. (2002). *Oncogene*, 21, 1812-22.

Spugnardi, M., Tommasi, S., Dammann, R., Pfeifer, G. P. & Hoon, D. S. (2003). *Cancer Res*, 63, 1639-43.

Takeuchi, H., Kuo, C., Morton, D. L., Wang, H. J. & Hoon, D. S. (2003). *Cancer Res*, 63, 441-8.

Toyota, M. & Issa, J. P. (1999). *Semin Cancer Biol*, 9, 349-57.

Umetani, N., Fujimoto, A., Takeuchi, H., Shinozaki, M., Bilchik, A. J. & Hoon, D. S. (2004a). *Oncogene*, 23, 8292-300.

Umetani, N., Takeuchi, H., Fujimoto, A., Shinozaki, M., Bilchik, A. J. & Hoon, D. S. (2004b). *Clin Cancer Res*, 10, 7475-83.

Welcsh, P. L., Lee, M. K., Gonzalez-Hernandez, R. M., Black, D. J., Mahadevappa, M., Swisher, E. M., Warrington, J. A. & King, M. C. (2002). *Proc Natl Acad Sci USA*, 99, 7560-5.

Zebedee, Z. & Hara, E. (2001). Oncogene, 20, 8317-25.

---

What is claimed is:

1. A method of determining whether a human subject is suffering from or at risk for developing colorectal cancer, comprising: obtaining a biological sample from a human subject; and determining the methylation level of an ID4 gene promoter in the sample, wherein the methylation level of the ID4 gene promoter in the sample, if higher than a control methylation level, indicates that the human subject is likely to be suffering from or at risk for developing colorectal cancer.

2. The method of claim 1, wherein the subject is likely to be suffering from or at risk for developing primary or metastatic colorectal cancer.

3. The method of claim 1, wherein the methylation level of the ID4 gene promoter is determined by methylation-specific PCR, bisulfite sequencing, or a combination thereof.

4. A method of determining the histopathological grade of human colorectal cancer, comprising: obtaining a biological sample from a human subject suffering from or suspected of suffering from early stage colorectal cancer; determining the methylation level of an ID4 gene promoter in the sample and correlating the methylation level of the ID4 gene promoter in the sample to a histopathological grade of the colorectal cancer.

5. The method of claim 4, wherein the sample is a benign or primary colorectal tumor specimen sample.

6. A method of predicting the outcome of colorectal cancer or breast cancer, comprising: obtaining a biological sample from a human subject suffering from colorectal cancer or breast cancer; determining the methylation level of an ID4 gene promoter in the sample and correlating the methylation level of the ID4 gene promoter in the sample to an outcome of the colorectal cancer or breast cancer.

7. The method of claim 6, wherein the subject is suffering from or at risk for developing American Joint Committee on Cancer stage I, II, III, or IV cancer.

8. The method of claim 6 wherein the sample is a primary tumor sample.

9. The method of claim 6 wherein the methylation level of the ID4 gene promoter is determined by methylation-specific PCR, bisulfite sequencing, or a combination thereof 10. The method of claim 6 wherein the outcome is the survival of the subject after a surgical resection.

11. The method of claim 10, wherein the surgical resection is a curative surgical resection.

12. A method of determining whether a human subject having breast cancer or colorectal cancer is suffering from or at risk for developing metastasis, comprising: obtaining a biological sample from a human subject having breast cancer or colorectal cancer or at risk for developing breast or colorectal cancer; and determining the methylation level of an ID4 gene promoter in the sample wherein the methylation level of the ID4 gene promoter in the sample, if higher than a control methylation level, indicates that the human subject is likely to be suffering from or at risk for developing metastasis.

13. The method of claim 12, wherein the sample is a benign lesion sample or an early stage primary tumor sample.

14. The method of claim 12 wherein the methylation level of the ID4 gene promoter is determined by methylation-specific PCR, bisulfite sequencing, or a combination thereof.

15. The method of claim 12, wherein the metastasis is Lymph node metastasis.

16. The method of claim 12, wherein the sample is a T1, T2, or T3 breast cancer sample.

* * * * *

SEQUENCE LISTING

```
<160> NUMBER OF SEQ ID NOS: 9

<210> SEQ ID NO 1
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 1
ttttataaat atagttgcgc ggc                                          23

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 2
gaaactccga ctaaacccga t                                            21

<210> SEQ ID NO 3
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 3
ttttataaat atagttgtgt ggtgg                                        25

<210> SEQ ID NO 4
<211> LENGTH: 23
<212> TYPE: DNA
```

```
<213> ORGANISM: Artificial sequence
<220> FEATURE:
<223> OTHER INFORMATION: Synthetic oligonucleotide

<400> SEQUENCE: 4
tcaaaactcc aactaaaccc aat                                                23

<210> SEQ ID NO 5
<211> LENGTH: 37
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(25)
<223> OTHER INFORMATION: Y = C or T

<400> SEQUENCE: 5
ttttattygg gtagtyggat ttttygtttt ttagtat                                 37

<210> SEQ ID NO 6
<211> LENGTH: 29
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: R = G or A

<400> SEQUENCE: 6
cccacccraa tatcctaatc actcccttc                                          29

<210> SEQ ID NO 7
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 7
cgctcactgc gctcaacac                                                     19

<210> SEQ ID NO 8
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 8
tcaggcggcc gcacacct                                                      18

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
cattctgtgc cgctgagccg                                                    20
```